US011945771B1

(12) United States Patent
Demmelmaier-Chang et al.

(10) Patent No.: US 11,945,771 B1
(45) Date of Patent: Apr. 2, 2024

(54) CATALYZED DEPOLYMERIZATION OF A CHEMICALLY COMPLEX FEEDSTOCK

(71) Applicant: Chevron Phillips Chemical Company LP, The Woodlands, TX (US)

(72) Inventors: Cori Demmelmaier-Chang, Houston, TX (US); Mark L. Hlavinka, Kingwood, TX (US); Sikander Hakim, Kingwood, TX (US); Gabriela Alvez, Kingwood, TX (US); Joseph Bergmeister, Spring, TX (US); Steven Lim, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/051,718

(22) Filed: Nov. 1, 2022

(51) Int. Cl.
*C07C 4/22* (2006.01)

(52) U.S. Cl.
CPC ............ *C07C 4/22* (2013.01); *C07C 2529/06* (2013.01)

(58) Field of Classification Search
CPC .............................. C07C 4/22; C07C 2529/06
See application file for complete search history.

(56) References Cited

U.S. PATENT DOCUMENTS

| 5,079,385 | A | 1/1992 | Wu |
| 9,802,184 | B2 | 10/2017 | Ramesh |
| 10,513,661 | B2 | 12/2019 | Narayanaswamy |
| 2014/0228606 | A1 | 8/2014 | Narayanaswamy |
| 2019/0299491 | A1 | 10/2019 | Stanislaus |
| 2021/0070958 | A1 | 3/2021 | Brita |
| 2021/0070959 | A1* | 3/2021 | Brita ...................... C08J 11/16 |
| 2021/0363432 | A1 | 11/2021 | Bitting |
| 2022/0176358 | A1 | 6/2022 | Nagy |

FOREIGN PATENT DOCUMENTS

| EP | 3744814 A1 | 12/2020 |
| EP | 4032963 A1 | 7/2022 |
| WO | 2020104385 A1 | 5/2020 |
| WO | 2021236971 A1 | 11/2021 |
| WO | 2022144616 A1 | 7/2022 |

OTHER PUBLICATIONS

Conk, et.al., "Catalytic deconstruction of waste polyethylene with ethylene to form propylene", Science, Sep. 29, 2022, vol. 377, Issue 6614, pp. 1561-1566. DOI: 10.1126/science.add1088.

(Continued)

*Primary Examiner* — Thuan D Dang
(74) *Attorney, Agent, or Firm* — Eversheds Sutherland (US) LLP

(57) ABSTRACT

Depolymerization processes and systems for converting polyolefin waste and other waste plastic to hydrocarbons, specifically liquid and gaseous depolymerization reaction products. A depolymerization or catalytic pyrolysis process can be conducted on a process feed which includes a polyolefin waste and a hydrocarbon co-feed under depolymerization conditions, including contacting the reactor feed with a depolymerization catalyst such as a zeolite-based catalyst. The resulting reactor effluent subsequently can be used as feeds or co-feeds for making circular products such as circular ethylene and circular polyethylene.

38 Claims, 1 Drawing Sheet

(56) References Cited

OTHER PUBLICATIONS

Costa, et al., "H-USY and H-ZSM-5 zeolites as catalysts for HDPE conversion under a hydrogen reductive atmosphere", Sustainable Energy Fuels, 2021,5, 1134-1147. DOI:10.1039/D0SE01584A.

Ellis, et. al., "Tandem Heterogeneous Catalysis for Polyethylene Depolymerization via an Olefin-Intermediate Process", ACS Sustainable Chem. Eng. 2021, 9, 623-628, Jan. 8, 2021. DOI:10.1021/acssuschemeng.0c07612.

Jaydev, Direct Conversion of Polypropylene into Liquid Hydrocarbons on Carbon-Supported Platinum Catalysts', ChemSusChem 2021, 14. doi.org/10.1002/cssc.202101999.

Liu, et.al., "Plastic waste to fuels by hydrocracking at mild conditions", Sci. Adv. 7 (17),: eabf8283, Apr. 21, 2021. DOI: 10.1126/sciadv.abf8283.

Miskolczi, N, et. al. "Preparation And Application Of Metal Loaded ZSM-5 and Y-Zeolite Catalysts For Thermo-Catalytic Pyrolysis Of Real End Of Life Vehicle Plastics Waste", Journal Of The Energy Institute, 92 (1): p. 118-127, Feb. 2019. https://doi.org/10.1016/j.joei.2017.10.017.

Santos, BPS, et. al. "Petrochemical Feedstock From Pyrolysis Of Waste Polyethylene And Polypropylene Using Different Catalysts", Fuel, 215: p. 515-521, Mar. 1, 2018. https://doi.org/10.1016/j.fuel.2017.11.104.

WANG et.al., "Chemical Recycling of Polyethylene by Tandem Catalytic Conversion to Propylene", J. Am. Chem. Soc. Sep. 30, 2022, https://doi.org/10.1021/jacs.2c07781.

Zhang, et al., "Polyethylene upcycling to long-chain alkylaromatics by tandem hydrogenolysis/aromatization", Science 370, 437-441 (Oct. 23, 2020). DOI: 10.1126/science.abc5441.

International Search Report and Written Opinion issued in corresponding PCT Application No. PCT/US2023/077132, dated Feb. 9, 2024, 16 pp.

* cited by examiner

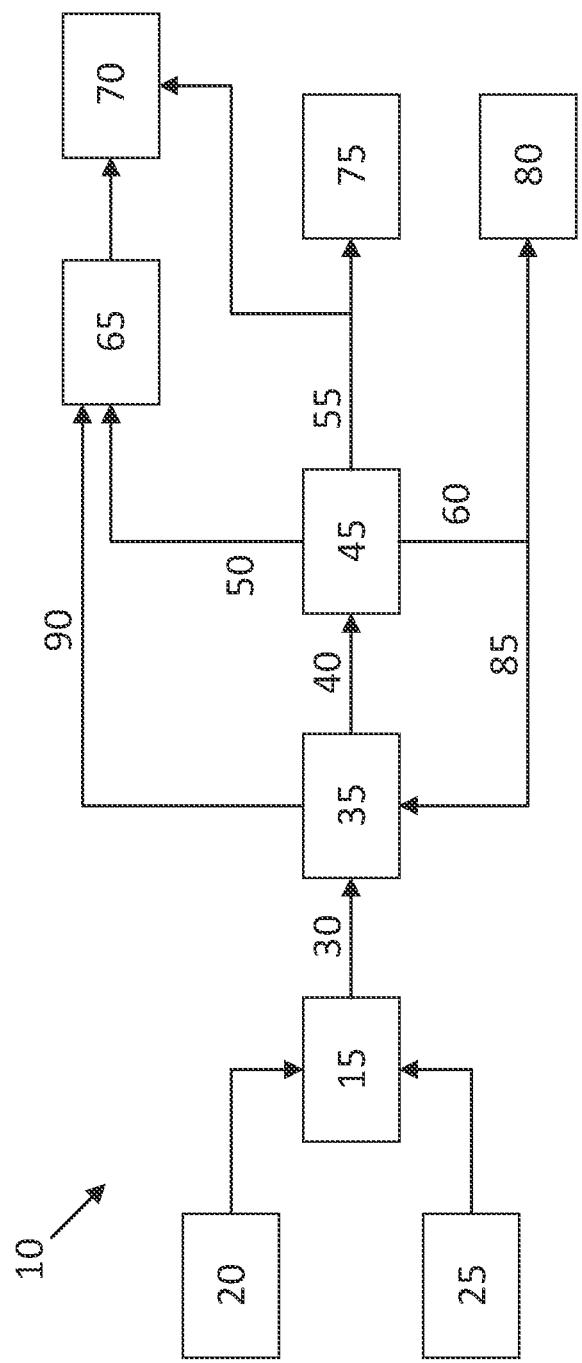

CATALYZED DEPOLYMERIZATION OF A CHEMICALLY COMPLEX FEEDSTOCK

CROSS REFERENCE TO RELATED APPLICATIONS

None.

TECHNICAL FIELD

This disclosure relates to the catalytic depolymerization of polyolefin waste and other waste plastic to provide hydrocarbon streams which can be used as feeds or co-feeds for the synthesis of circular chemicals and polymers.

BACKGROUND OF THE DISCLOSURE

The worldwide environmental impact associated with discarded plastic waste products is substantial, and the need to recycle plastic wastes is urgent. However, there are significant and persistent problems in conventional recycling methods for some plastics. The melts generated from mixed plastic waste include a range of plastic types that tend to separate into different phases. This phase separation results in structural weakness in the recycled product, and a significant proportion of virgin plastic must usually be blended in to impart the necessary physical properties to the product such as impact strength, tensile strength, and resistance to environmental stress cracking to name a few.

An alternative recycling method which is potentially more economically viable for mixed plastic waste is feedstock recycling using pyrolysis of these plastic waste materials. In these processes, plastic waste materials are pyrolyzed into a liquid hydrocarbon product referred to as pyrolysis oil, which can be recycled using petrochemical processing methods to produce a feedstock or co-feedstock for various processing units, including processing units which produce the monomers from which these same polymers can be produced from again. However, current pyrolysis methods produce a pyrolysis oil which includes a broad distribution of hydrocarbon molecular weights. Moreover, conventional pyrolysis reactor designs and operating conditions tend to produce an undesirably high proportion of a heavy waxy fraction, which forms solids at ambient temperatures and can require additional processing and increases costs, before the pyrolysis product is suitable as a feed or co-feed in a refinery or chemical plant.

Therefore, what is needed are new or improved processes and systems which can limit or avoid the disadvantages associated with conventional pyrolysis methods without requiring extensive sorting of the incoming plastic waste. In particular, processes and systems which could avoid traditional pyrolysis and obviate the need for refinery processes yet utilize recycled plastic feedstock to access C—C bonds as a feed or co-feed in a chemical plant to create circular chemicals and plastics would be desirable.

SUMMARY OF THE DISCLOSURE

This disclosure provides for new depolymerization processes and systems for converting plastic wastes to hydrocarbons, specifically liquid and gaseous depolymerization products, which subsequently can be used as feeds or co-feeds for making circular products such as circular ethylene and circular polyethylene. It has been discovered that an efficient and useful depolymerization or "catalytic pyrolysis" process can be conducted on a process feed which includes a polyolefin waste feed and a hydrocarbon co-feed to form a feed for the depolymerization process in a reactor. When this reactor feed is then fed to the depolymerization reactor and its heating zone where it is heated and contacted with a depolymerization catalyst under suitable depolymerization conditions, a reactor effluent is formed which can be separated into useful output streams comprising circular products. In an aspect, the initial heating of the process feed or the subsequent heating under depolymerization conditions can be conducted in the presence of a chemically-modified solid oxide, which includes a solid oxide treated with an electron-withdrawing anion.

The Applicant has found that this process for depolymerization of polymers such as polyethylene using a depolymerization catalyst such as a zeolite-based catalyst or chromia catalyst can be readily conducted in a fluidized or a fixed bed depolymerization (catalyzed pyrolysis) reactor, and the resulting product can be separated into different product or output streams. The output streams from the separation steps can include, for example, $C_2$-$C_5$ hydrocarbons, $C_6$-$C_8$ hydrocarbons, or $C_{9+}$ hydrocarbons. In an aspect, $C_2$-$C_5$ saturated and unsaturated hydrocarbons can be provided to a steam cracker to produce circular ethylene and/or circular propylene. The $C_6$-$C_8$ hydrocarbons can be provided to, for example, a reforming unit or an AROMAX® unit or provided to a steam cracker to produce circular ethylene and/or circular propylene. In an aspect, the $C_{9+}$ heavies product can be recycled to the depolymerization reactor for heating in the presence of the depolymerization catalyst.

In aspect, the depolymerization catalyst for converting the plastic waste can comprise, consist essentially of, or can be a zeolite-based catalyst, a chromia-based catalyst, or a combination thereof. For example, the depolymerization catalyst can be a zeolite-based catalyst such as a Pt/zeolite catalyst with the zeolite being any zeolite including L-zeolite or ZSM-5 (MFI) zeolite. The depolymerization catalysts of this disclosure are utilized for their dehydrogenation, hydrogenolysis, cracking, and isomerization functions to depolymerize the polyolefin in the liquid reactor feed. The process can be optimized or adjusted toward the production of selected products for producing circular chemical and polymer products downstream. For example, using a Pt/zeolite catalyst as described herein can be optimized to favor $C_2$-$C_8$ products which can be separated and fed to olefin cracker and/or AROMAX® Process. Catalyst properties can be adjusted if desired, for example, by selecting the zeolite pore volume and zeolite pore diameter, by enhancing catalyst acidity, or by utilizing promoters to tailor the product distribution in the depolymerization effluent.

Therefore, in one aspect, this disclosure provides a process for converting plastic waste, in which the process can comprise:

(a) providing a process feed comprising a polyolefin waste to a first heating zone and heating the process feed;

(b) combining a hydrocarbon co-feed with the process feed to form a reactor feed;

(c) providing the reactor feed to a second heating zone and heating the reactor feed in the presence of a depolymerization catalyst under depolymerization conditions to form a reactor effluent; and (d) separating the reactor effluent into a plurality of output streams, each output stream comprising a circular product.

The process feed which comprises a polyolefin waste and can include other waste plastics as well. In embodiments, the hydrocarbon co-feed can comprise or can be selected from a pyrolysis oil, a pyrolysis oil fraction, a petroleum-based co-feed, a fossil fuel-based co-feed, or a bio-based co-feed.

According to another aspect, this disclosure provides a system for converting plastic waste, in which the system can comprise:

(a) a first heating zone configured to receive a process feed and optionally receive a first hydrocarbon co-feed, and heat the process feed to provide a reactor feed;

(b) a depolymerization reactor comprising a first feed inlet configured to receive the reactor feed, a second heating zone, and at least one outlet configured to discharge a reactor effluent, and configured to contact the reactor feed with a depolymerization catalyst under depolymerization conditions; and (c) a separation unit, configured to receive and separate the reactor effluent into a plurality of output streams, each output stream comprising a circular product.

In embodiments, the separation unit can comprise one or more condensers downstream of the depolymerization unit configured to separate the reactor effluent into the plurality of output streams. The plurality of output streams can comprise, for example, a light hydrocarbon stream ($C_2$-$C_5$), a medium hydrocarbon stream ($C_6$-$C_8$), a heavy hydrocarbon stream ($C_{9+}$), or any combination thereof.

These and other aspects, embodiments, and improvements are described more fully in the Detailed Description, the listed Aspects, the claims, and the further disclosure such as the Examples and Drawings provided herein.

BRIEF DESCRIPTION OF THE DRAWINGS

FIG. 1 illustrates aspects of the disclosure showing an exemplary embodiment of a system and process for converting plastic waste for the production of circular products. Illustrated are a heating unit comprising a first heating zone and configured to receive a process feed that includes a polyolefin waste and heat the process feed. A hydrocarbon co-feed may be combined with the process feed at various stages including in the first heating zone as illustrated in this embodiment, where the process feed and the hydrocarbon co-feed are combined to form the reactor feed. The reactor feed is fed to the depolymerization reactor comprising a second heating zone where the feed is contacted with a depolymerization catalyst under depolymerization conditions to form a reactor effluent, which can be separated into a plurality of output streams.

DETAILED DESCRIPTION OF THE DISCLOSURE

This disclosure provides depolymerization or "catalytic pyrolysis" processes and systems for converting polymer waste to smaller hydrocarbons, specifically liquid and gaseous depolymerization reactor products, which subsequently can be modified and used as feeds or co-feeds for making circular products like circular ethylene and polyethylene. In an aspect, this process for depolymerizing polymers such as polyethylene can use a depolymerization catalyst such as a zeolite-based catalyst and can optionally use a chemically-modified solid oxide comprising a solid oxide treated with an electron withdrawing anion. The depolymerization products subsequently can be separated into various product streams and used to make circular chemical and polymer products. These processes and systems can expand the number of usable plastic waste streams and improve the economics of plastic waste recycling.

Definitions

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in Chemical and Engineering News, 63(5), 27, 1985. In some instances, a group of elements may be indicated using a common name assigned to the group; for example alkali metals for Group 1 elements, alkaline earth metals for Group 2 elements, transition metals for Group 3-12 elements, and halogens or halides for Group 17 elements.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Unless specified to the contrary, describing a process, system, or composition as "consisting essentially of" is not to be construed as "comprising," but is intended to describe the recited component that includes materials which do not significantly alter or do not materially affect the basic and novel characteristic(s) of process, system or composition to which the term is applied. For example, a feedstock consisting essentially of a material A can include impurities typically present in a commercially produced or commercially available sample of the recited material A.

When a claim includes different features and/or feature classes (for example, process steps, feedstock features, and/or product features, among other possibilities), the transitional terms comprising, consisting essentially of, and consisting of, apply only to feature class to which is utilized and it is possible to have different transitional terms or phrases utilized with different features within a claim. For example, a method can comprise several recited steps (and other non-recited steps) but utilize a catalyst composition preparation consisting of specific steps but utilize a catalyst composition comprising recited components and other non-recited components. While compositions and methods are described in terms of "comprising" various components or steps, the compositions and methods can also "consist essentially of" or "consist of" the various components or steps, unless stated otherwise.

The terms "a," "an," and "the" are intended, unless specifically indicated otherwise, to include plural alternatives, e.g., at least one. For instance, the disclosure of "a heating zone" or a "heater" is meant to encompass one heating zone (or heater) or more than one heating zone (or heater) unless otherwise specified.

The terms "configured for use" or "adapted for use" and similar language is used herein to reflect that the particular recited structure or procedure is used in depolymerization (catalytic pyrolysis) system or process, or in a system or process downstream thereof such as an olefin polymerization system or process. For example, unless otherwise specified, a particular structure "configured for use" means it is "configured for use in a depolymerization reactor system" and therefore is designed, shaped, arranged, constructed, and/or tailored to effect depolymerization, as would have been understood by the skilled person.

For any particular compound disclosed herein, a general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise or unless the context provides or requires otherwise. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicant states that one or more steps in the processes disclosed herein can be conducted at a temperature in a range from 10° C. to 75° C., this range should be interpreted as encompassing temperatures in a range from "about" 10° C. to "about" 75° C.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual process steps, reactor elements, chemical substituents, analogs, compounds, ligands, structures, or groups thereof, or any members of a claimed group, if for any reason Applicant chooses to claim less than the full measure of the disclosure.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, use of the term "about" can mean ±15% of the stated value, ±10% of the stated value, ±5% of the stated value, ±3% of the stated value, ±2% of the stated value, or ±1% of the stated value.

The term "olefin" is used herein in accordance with the definition specified by IUPAC: acyclic and cyclic hydrocarbons having one or more carbon-carbon double bonds apart from the formal ones in aromatic compounds. The class "olefins" subsumes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise.

The term "polymer" is used herein generically to include homopolymers, copolymers, terpolymers, and so forth, such as olefin homopolymers, copolymers, terpolymers, and the like. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin polymer (polyolefin), such as an ethylene copolymer, can be derived from ethylene and a comonomer, such as 1-butene, 1-hexene, or 1-octene. If the monomer and comonomer were ethylene and 1-hexene, respectively, the resulting polymer could be categorized an as ethylene/1-hexene copolymer or a poly(ethylene-co-1-hexene) polymer.

In like manner, the scope of the term "polymerization" includes homopolymerization, copolymerization, terpolymerization, etc. Therefore, a copolymerization process could involve contacting one olefin monomer (e.g., ethylene) and one olefin comonomer (e.g., 1-hexene) to produce a copolymer.

The terms "light", "medium" and "heavy", unless defined otherwise or unless the context requires otherwise, are relative terms and are used herein to refer to the components of a process feed or process feed, a reactor effluent, a product from a separation system such as a condenser system, and the like. The "light", "medium" and "heavy" feeds, effluents, or products may constitute separate or combined feed streams, effluent streams, or products, as understood by the person of ordinary skill in the art according to the context in which these terms are used. For example, a depolymerization reactor effluent may include a gaseous effluent and a liquid effluent which may be referred to as simply "light" and "heavy", and products from a separation unit may include combinations of "light", "medium" and "heavy" products. Thus, depending upon the reactor and process conditions, the depolymerization reactor effluent can include: a light fraction and a heavy fraction; or a light fraction, one or more medium fractions, and a heavy fraction; and the like. Referring to portions of the depolymerization reactor effluent as light, medium, heavy, gaseous, or liquid are relative terms, and the carbon count or weight of the hydrocarbons constituting each fraction can depend upon factors such as the reactor conditions such as temperature and pressure and the type, the design, and the efficiency of the separation system. These descriptions of light, medium, and heavy components are approximate, and the light fraction may include some components found in the medium or heavy fraction, the medium fraction may include some components found in the light or heavy fraction, and the heavy fraction may include some components found in the light or medium fraction. As described further herein, if necessary for the definiteness of a claim or for other reasons, the "light fraction" can comprise primarily $C_2$-$C_5$ hydrocarbons, the "medium fraction" can comprise primarily $C_6$-$C_8$ hydrocarbons, and the "heavy fraction" can comprise primarily $C_{9+}$ hydrocarbons, unless otherwise provided. Moreover, the general terms "light", "medium", and "heavy" when referring to hydrocarbons, can be used to refer to compositions which comprise primarily $C_2$-$C_5$ hydrocarbons (light), primarily $C_6$-$C_8$ hydrocarbons (medium), and primarily $C_{9+}$ hydrocarbons (heavy). In a similar fashion, terms such as "light fraction gas", "light fraction liquid", and the like are relative terms, and the weight of the hydrocarbons constituting each portion can depend upon various factors such as the type, the design, and the efficiency of a separation unit.

The terms "halogen" and "halide" are used interchangeably in this disclosure, unless stated otherwise or unless the context requires otherwise, to refer to fluorine, chlorine, bromine, and iodine, regardless of whether these elements are in neutral or anionic form or occur as molecular or polymeric substituents or atoms in a solid-state structure. These terms are often used in the context of a halide or halogen contaminant that may occur in a polyolefin waste feed or a light hydrocarbon co-feed, in which these terms are used interchangeably.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Catalytic Depolymerization Process and System

An aspect of this disclosure utilizes a depolymerization or "catalytic pyrolysis" processes and systems for converting polymer waste to smaller hydrocarbons, specifically liquid and gaseous depolymerization products, which subsequently can be used as feeds or co-feeds for making circular products. The process for depolymerizing polymers such as polyethylene can use a depolymerization catalyst such as a zeolite-based catalyst or a chromia-based catalyst. Examples of a zeolite-based catalyst include a Pt/zeolite catalyst, in which the zeolite can comprise any zeolite such as L-zeolite or ZSM-5. Promoters can be used in combination with these catalysts, such as tin or optionally a solid super-acid or "SSA" (for example, sulfated alumina) for acidity.

Zeolite pore volume and zeolite pore diameter of the zeolite itself of the zeolite-based catalyst can be used to adjust or optimize the process for the desired hydrocarbon distribution and catalyst acidity, for example, to produce a maximum amount of the desired feedstock such as a $C_2$-$C_8$ feedstock. The depolymerization process can be conducted in a fluidized or fixed bed depolymerization (catalyzed pyrolysis) reactor, and the products subsequently can be separated into various product streams. For example, the depolymerization process effluent can be separated into a $C_2$-$C_5$ stream which can be fed to a steam cracker, a $C_6$-$C_8$ stream which can be fed to an AROMAX® unit, and a $C_{9+}$ heavies stream which can be recycled to the depolymerization reactor and process.

Accordingly, in an aspect, this disclosure provides a process for converting plastic waste, the process comprising:
(a) providing a process feed comprising a polyolefin waste to a first heating zone and heating the process feed;
(b) combining a hydrocarbon co-feed with the process feed to form a reactor feed;
(c) providing the reactor feed to a second heating zone and heating the reactor feed in the presence of a depolymerization catalyst under depolymerization conditions to form a reactor effluent; and
(d) separating the reactor effluent into a plurality of output streams, each output stream comprising a circular product.

The first heating zone is not limited to any specific type of heating unit, for example, the first heating zone can comprise an extruder. The process feed which includes the polyolefin waste feed is heated in the first heating zone, and the polyolefin waste is partially or completely melted. Combining a hydrocarbon co-feed with the process feed can occur before, during, or after providing the process feed to the first heating zone, or before, during, or after heating the process feed, or any combination thereof. Thus, the hydrocarbon co-feed can be combined with process feed prior to feeding to the first heating zone, while the process feed is being heated, or after the process feed has been heated to partially or completely melt the polyolefin waste. This process can also further include the step of introducing additional process feed, additional hydrocarbon co-feed, or both additional process feed and hydrocarbon co-feed into the depolymerization reactor if desired.

According to another aspect, the process for converting plastic waste can further comprise combining a depolymerization catalyst such as a zeolite-based catalyst with the process feed in the first heating zone. In a further aspect, the process can further comprise combining the depolymerization catalyst with the reactor feed before or after providing the reactor feed to the depolymerization reactor.

In one aspect, this process can further comprise recycling one or more of the output streams such as a heavy fraction, upstream to the depolymerization reactor. In this way, further depolymerization or deoligomerization can occur to provide the desired product distribution.

In this process for converting plastic waste, the process feed contains polyolefin waste, which may be referred to as a polyolefin waste feed, and the amount or the fraction of the circular product attributable to the polyolefin waste or any additional plastic waste in one or more output streams can be determined by mass balance. In one aspect, the process for converting plastic waste can further comprise certifying the circular product attributable to the polyolefin waste or the additional plastic waste in one or more output streams as Circular in accordance with International Sustainability and Carbon Certification (ISCC) standards, based upon the amount or the fraction of the circular product attributable to the polyolefin waste or the additional plastic waste in one or more output streams determined by mass balance and the free attribution method. In this aspect, these calculations to account for plastic waste can consider the polyolefin waste in the process feed and any polyolefin waste or other polymer wastes in the hydrocarbon co-feed.

Process Feed and Polyolefin Waste

In this process for converting plastic waste, the process feed can comprise a polyolefin waste such as a polyethylene, a polypropylene, a polystyrene, other polyolefins, or any combination thereof. Therefore, in an aspect, the process feed and/or the polyolefin waste is a solid at 25° C. While the process feed can include a high proportion of polyolefin waste materials, the process feed may also include other types of "waste plastic" or "plastic waste" which are different from the polyolefin waste. Therefore, the reactor feed formed after combining the hydrocarbon co-feed with the process feed can also comprise additional plastic waste which is different from the polyolefin waste. For example, in additional to the polyolefin waste, the process feed can include waste plastics such as polyesters, polyamides, polyurethanes, polyphenols, polycarbonates, polyvinyl chlorides, or any combinations thereof. Therefore, in an aspect, the waste plastics which can be used in the process feed also can be a solid at 25° C. In another aspect, the waste plastic can include polyethylene terephthalate (PET) or polyvinyl chloride (PVC), which are prevalent in waste plastics. When the waste plastic comprises polyvinyl chloride (PVC), the PVC can be present in the process feed in a concentration of less than 10 wt. %, less than 5 wt. %, less than 2 wt. %, less than 1 wt. %, or less than 0.5 wt. %. When the waste plastic comprises polyethylene terephthalate (PET), the PET can be present in the process feed in a concentration of less than 10 wt. %, less than 5 wt. %, less than 2 wt. %, less than 1 wt. %, or less than 0.5 wt. %.

In this aspect, the polyolefin waste can be present in the reactor feed, that is, in the combination of process feed and the hydrocarbon co-feed, in a concentration from greater than 0 wt. % or from about 15 wt. %, and up to 40 wt. %, 50 wt. %, 60 wt. %, 70 wt. %, or 80 wt. %. For example, the polyolefin waste can be present in the reactor feed in a concentration of from about 10 wt. % to about 80 wt. %, from about 15 wt. % to about 70 wt. %, or from about 20 wt. % to about 60 wt. %. These concentrations refer to those polymers traditionally recognized as polyolefins rather than halogenated polyolefins, therefore these concentrations would not include any polyvinyl chloride or polytetrafluoroethylene present in the feed. The polyolefin waste also may be present in the reactor feed in a concentration of about 5 wt. %, about 10 wt. %, about 20 wt. %, about 30 wt. %, about 40 wt. %, about 50 wt. %, about 60 wt. %, about 70 wt. %, about 80 wt. %, or any range between any of these weight percentages.

The process feed can consist essentially of or can be a polyolefin waste, without additional waste plastics or other components or compositions being present in the process feed. Thus, the process feed can be fed to the first heating zone as a solid having an average size range which is beneficial for handling and feeding the solid or slurry of the polyolefin in the hydrocarbon co-feed and beneficial to melting the solid process feed to form the liquid reactor feed. In this aspect, the process feed and/or the polyolefin waste can be a solid having an average particle size of less than or equal to 4 mm, less than or equal to 3 mm, less than or equal to 2 mm, less than or equal to 1 mm, or from about 1 mm to about 3 mm.

Hydrocarbon Co-Feed

In aspects, the depolymerization reactor and process feed can comprise a process feed and a hydrocarbon co-feed, and the hydrocarbon co-feed is not limited to any particular hydrocarbon. For example, the hydrocarbon co-feed can comprise a pyrolysis oil, a pyrolysis oil fraction, a petroleum-based co-feed, a fossil fuel-based co-feed, or a bio-based co-feed. The hydrocarbon co-feed can comprise a light hydrocarbon co-feed, a medium hydrocarbon co-feed, or a heavy hydrocarbon co-feed. In an aspect, the hydrocarbon co-feed can be a liquid or a solid at 25° C. (e.g., a wax). When the hydrocarbon co-feed comprises a pyrolysis oil, the determination of the fraction of any circular product can account for recycled mass from the polyolefin waste and from the pyrolysis oil which is attributable to plastic waste.

In an aspect, the hydrocarbon co-feed which is heated along with the process feed can comprise or can be selected from a pyrolysis oil, a pyrolysis oil fraction, a $C_5$-$C_6$ saturated hydrocarbon, natural gas liquids (NGL), light naphtha, heavy naphtha, or combinations thereof. When the hydrocarbon co-feed comprises or is selected from a pyrolysis oil, the pyrolysis oil can be derived from the pyrolysis of a range of different waste polymers, such as polyethylene, polypropylene, polystyrene, polyethylene terephthalate (PET), polyvinyl chloride (PVC), polyamide, polycarbonate, polyurethane, polyester, copolymers thereof, filled polymers thereof, composites thereof, natural or synthetic rubber, tires, or any combination thereof.

In embodiments, if desired, the reactor feed which is heated and in particular the hydrocarbon co-feed can include a natural or a synthetic antioxidant which can be combined with the co-feed. In an aspect, the antioxidant can be: (a) compliant with at least one of the Gulf Cooperation Council Standardization Organization GSO 2231/2012, GSO 839/1997, or GSO 1863/2013 standard; or (b) Halal certified, Kosher certified, or HACCP certified. The antioxidant also may comprise a hindered phenol, a metal salt of a hindered phenol, an oil-soluble polymetal organic compound, a hindered phenylenediamine compound, or a combination thereof.

In aspects, the reactor feed or the hydrocarbon co-feed can include an antioxidant which comprises or can be selected from diphenylamines, phenyl naphthylamines, phenothiazines, imidodibenzyls, diphenyl phenylene diamines, aromatic amines, or combinations thereof. For example, the antioxidant can comprises or can be selected from 2-t-butyl-4-heptyl phenol, 2-t-butyl-4-octyl phenol, 2-t-butyl-4-dodecyl phenol, 2,6-di-t-butyl-4-methylphenol, 2,6-di-t-butyl-4-heptyl phenol, 2,6-di-t-butyl-4-dodecyl phenol, 2-methyl-6-t-butyl-4-heptyl phenol, 2-methyl-6-t-butyl-4-dodecyl phenol, 2,6-di-alkyl-phenolic propionic ester derivatives, 2,2'-bis(4-heptyl-6-t-butyl-phenol), 2,2'-bis(4-octyl-6-t-butyl-phenol), 2,2'-bis(4-dodecyl-6-t-butyl-phenol), 4,4'-bis(2,6-di-t-butyl phenol), 4,4'-methylene-bis(2,6-di-t-butyl phenol), 2-t-butyl-4-methoxyphenol, 3-t-butyl-4-methoxyphenol, propyl gallate, 2-(1,1-dimethylethyl)-1,4-benzenediol, p,p'-dioctyldiphenylamine, t-octylphenyl-α-naphthylamine, phenyl-α-naphthylamine, p-octylphenyl-α-naphthylamine, or combinations thereof.

In a further aspect, the reactor feed or the hydrocarbon co-feed can include an antioxidant which comprises or can be selected from olive plant materials, olive oil, olive leaf extracts, a sesame-based antioxidant, sesamol, sesamin, sesamolin, hydroxytyrosol, tyrosol, caffeic acid, ferulic acid, alkannin, shikonin, carnosic acid, carnosic acid-EDTA, α-tocopherol (TCP), propyl gallate (PG), 1-ascorbic acid 6-palmitate (AP), gallic acid, quercetin, myricetin, catechin, genistein, isoflavones, flavanols, cinnamic acid, hydroxtycinnamic acid, oleuropein, oryzanols, tocols, β-carotene, carotenoids, lycopene, marigold, paprika, bixin, or any combination thereof. In embodiments, the antioxidant can comprise or can be selected from an antioxidant derived from olive plant material, olive oil mill waste, ajowan (*Carum copticum*), *tinctoria* roots, rosemary extract, *Guiera senegalensis, Combretum hartmannianum, Majorana syriaca*, sesame, *Artmisia scoparia, Cinnamomum cassia*, rosemary (Rosemarinus *officinalis*), clove (*Syzygium aromaticum*), cinnamon (*Cinnamomum zeylanicum*), broccoli, citrus, chemlali olive, defatted rice brand, bene hull oil (unsaponifiable matter), oregano, green tea, Cortex *fraxini, Polygonum cuspidatum*, marigold, *Capsicum annuum*, and garlic.

Heating and Depolymerization Conditions

Once the process feed is provided to the first heating zone it is heated, and the process feed can be combining with the hydrocarbon co-feed before, during, or after heating the process feed, or any combination thereof. Thus, the hydrocarbon co-feed can be combined with polyolefin prior to feeding to the first heating zone, while the process feed is being heated, or after the polyolefin waste has been heated and melted. The term "reactor feed" is used for the combination of the process feed including the polyolefin waste and the hydrocarbon co-feed regardless of at what stage or how the combining step occurs and regardless of the melt state of the polyolefin waste. The term "liquid reactor feed" may be used to refer to the reactor feed after the polyolefin waste has partially melted or completely melted.

The heating conditions required to melt the process feed and/or polyolefin waste are affected by the characteristics of the polyolefin itself, but generally the process feed or the reactor feed can be heated to a temperature of from about 150° F. (66° C.) to about 350° F. (177° C.), from about 170° F. (77° C.) to about 300° F. (149° C.), or from about 190° F. (88° C.) to about 280° F. (138° C.) in the first heating zone to form the liquid reactor feed. In this aspect, the process feed or the reactor feed can be heated to a temperature of about 150° F. (66° C.), about 160° F. (71° C.), about 170° F. (77° C.), about 180° F. (82° C.), about 190° F. (88° C.), about 200° F. (93° C.), about 210° F. (99° C.), about 220° F. (104° C.), about 230° F. (110° C.), about 240° F. (116° C.), about 250° F. (121° C.), about 260° F. (127° C.), about 270° F. (132° C.), about 280° F. (138° C.), about 290° F. (143° C.), about 300° F. (149° C.), about 310° F. (154° C.), about 320° F. (160° C.), about 330° F. (166° C.), about 340° F. (171° C.), or about 350° F. (177° C.) in the heating zone, or any range between any of these temperatures, to form the liquid reactor feed. In a further aspect, the process feed can be heated in the first heating zone to a temperature that is 15° F. (8° C.) to 50° F. (28° C.) below the boiling temperature of the hydrocarbon co-feed. Because the process feed can include a range of different solid polyolefins or other plastic waste products in addition to the solid polyolefin, the heating will occur over a range of temperatures, up to or slightly higher than the temperature at which the highest melting temperature solid will melt.

Regarding the depolymerization conditions, the depolymerization conditions can comprise heating the reactor feed in the second heating zone while contacting the reactor feed and the depolymerization catalyst. In an aspect, the depolymerization conditions can comprise heating the reactor feed in the second heating zone to a temperature of from 300° F. (149° C.) to 1,000° F. (538° C.), from 400° F. (204° C.) to 900° F. (482° C.), or from 450° F. (232° C.) to 800° F. (427° C.) while contacting the reactor feed and the depolymerization catalyst. For example, the depolymerization conditions comprise heating the reactor feed in the second heating zone to a temperature of about 300° F. (149° C.), about 350° F. (177° C.), about 400° F. (204° C.), about 450° F. (232° C.), about 500° F. (260° C.), about 550° F. (188° C.), about 600° F. (316° C.), about 650° F. (343° C.), about 700° F. (371° C.), about 750° F. (399° C.), about 800° F. (427° C.), about 850° F. (454° C.), about 900° F. (482° C.), about 950° F. (510° C.), about 1000° F. (538° C.), or any range between any of these temperatures, while contacting the reactor feed and the depolymerization catalyst.

In another aspect, the step of contacting the reactor feed and the depolymerization catalyst can be conducted in the presence of hydrogen. In this aspect, this step of contacting the reactor feed and the depolymerization catalyst can be conducted in the presence of hydrogen at a pressure of from about 5 psig (34 kPa) to about 1,000 psig (6895 kPa), from about 50 psig (335 kPa) to about 800 psig (5516 kPa), or from about 100 psig (689 kPa) to about 650 psig (4482 kPa). For example, contacting the reactor feed and the depolymerization catalyst is conducted in the presence of hydrogen at a pressure of about 5 psig (34 kPa), about 25 psig (172 kPa), about 50 psig (335 kPa), about 100 psig (689 kPa), about 150 psig (1034 kPa), about 200 psig (1379 kPa), about 250 psig (1724 kPa), about 300 psig (2068 kPa), about 350 psig (2413 kPa), about 400 psig (2758 kPa), about 450 psig (3103 kPa), about 500 psig (3447 kPa), about 550 psig (3792 kPa), about 600 psig (4137 kPa), about 650 psig (4482 kPa), about 700 psig (4826 kPa), about 750 psig (5171 kPa), about 800 psig (5516 kPa), about 850 psig (5861 kPa), about 900 psig (6205 kPa), about 950 psig (6550 kPa), about 1000 psig (6895 kPa), or any range between any of these pressures. However, the depolymerization conditions can include heating the reactor feed and the depolymerization catalyst in the second heating zone in the absence of hydrogen.

Halogen Concentration Control

In some instances, the reactor feed which includes the process feed the hydrocarbon co-feed may include undesirable polymers or contaminants which may adversely affect the depolymerization process or downstream processes in which the depolymerization process effluent eventually is used. In an aspect, the halogen concentrations in the process feed or the hydrocarbon co-feed can provide undesirable halogen-containing components in the depolymerization reactor and process effluent. Therefore, it may be desirable to control the halogen concentration in the reactor feed. For example, the halogen concentration in the process feed, the hydrocarbon co-feed, or both the process feed and the hydrocarbon co-feed can be controlled.

In embodiments, the removal or reduction in the concentrations of these halogen-containing components may be conducted. However, in some instances, the presence of halogens in the polyolefin or the hydrocarbon co-feed, particularly chlorine and fluorine, may be useful for controlling or maintaining the halogen concentration in a zeolite-based depolymerization catalyst to a desirable level. Therefore, controlling the halogen concentration of any feed streams to the second heating zone in the depolymerization reactor where the reactor feed contacts the depolymerization catalyst can be conducted.

There are several ways to control the halogen concentration of the reactor feed. For example, the halogen concentration of any materials used in making up the feed stream can be controlled or limited, and/or the halogens may be removed to the desired halogen concentration before the feed stream enters the depolymerization reactor. In an aspect, the halogen concentration in the reactor feed can be controlled by reducing the amount of halogen-containing polyolefin such as polyvinyl chloride or polytetrafluoroethylene in the process feed. In another aspect, the halogen concentration in the reactor feed can be controlled by reducing the amount of halogen-containing materials in the hydrocarbon co-feed, which can include pyrolysis oil and other materials made from recycled plastics. In embodiments, the halogen concentration can be controlled by treating the hydrocarbon co-feed or the reactor feed to reduce or remove halogens from these liquid materials.

In embodiments, the halogen concentration in the reactor feed also may be controlled. For example, the halogen concentration in the process feed, the hydrocarbon co-feed, or both the process feed and the hydrocarbon co-feed can be controlled. In another aspect, any additional materials used in making up the reactor feed either before it is heated or after it is heated to form the reactor feed can be controlled. All of these embodiments can be useful for halogen concentration control in the reactor feed which contacts the depolymerization catalyst such as a zeolite-based catalyst.

In one aspect, the chlorine or fluorine concentrations by weight in the reactor feed, independently, can be less than 100 ppm, less than 90 ppm, less than 80 ppm, less than 70 ppm, less than 60 ppm, less than 50 ppm, less than 40 ppm, less than 30 ppm, less than 20 ppm, less than 10 ppm, or less than 5 ppm. In another aspect, the chlorine or fluorine concentrations by weight in the reactor feed, independently, can be from 5 pm to 100 ppm, from 10 ppm to 80 ppm, or from 20 ppm to 80 ppm.

In a further aspect, the halogen concentration in the process feed, the hydrocarbon co-feed, or the reactor feed can be controlled to provide a halogen concentration in a zeolite-based depolymerization catalyst of less than 10 wt. %, less than 7 wt. %, less than 5 wt. %, less than 4 wt. %, less than 3 wt. %, less than 2 wt. %, or less than less than 1 wt. %. Because both fluoride concentrations and chloride concentrations can affect the performance of the zeolite-based depolymerization catalyst, either or both concentrations can be controlled. In an aspect, the halogen concentration in the process feed, the hydrocarbon co-feed, and/or the reactor feed can be controlled to provide a chloride concentration in the zeolite-based catalyst of from 0.1 wt. % to 4.0 wt. %. In another aspect, the halogen concentration in the process feed, the hydrocarbon co-feed, and/or the reactor feed can be controlled to provide a fluoride concentration in the zeolite-based catalyst of from 0.1 wt. % to 5.0 wt. %.

Depending upon the halide concentrations in the feed and co-feed streams and the extent to which these halide concentrations are used to maintain the halogen concentration in the zeolite-based depolymerization catalyst, the one or more output streams from the depolymerization reactor and the second heating zone can comprise halogenated hydrocarbons in a first concentration. Therefore, the disclosed process can further include the step of contacting the one or more output streams with a dehydrohalogenation catalyst to reduce the first concentration of halogenated hydrocarbons to a second concentration which is less than the first concentration.

In an aspect, the dehydrohalogenation catalyst comprises or is selected from a Group 4-13 metal supported on a metal oxide or aluminosilicate support, or a Group 4-13 metal supported on a metal oxide or aluminosilicate support, or a Group 6-11 metal supported on a metal oxide or aluminosilicate support. In embodiments, the dehydrohalogenation catalyst can comprise chromium, molybdenum, tungsten, iron, ruthenium, osmium, cobalt, rhodium, iridium, nickel, palladium, platinum, zinc, magnesium, gallium, titanium, tantalum, or any combination thereof, supported on alumina, silica, silica-alumina, silica-coated alumina, titania, zirconia, a zeolite, a molecular sieve, aluminophosphate, or a combination thereof.

Depolymerization Catalysts

In the disclosed process for converting plastic wastes, the reactor feed is heated and contacted with a depolymerization catalyst in a second heating zone under depolymerization conditions, to form a reactor effluent. The depolymerization catalyst can comprise any depolymerization catalyst, for example, a zeolite-based catalyst, a chromia-based catalyst, or a combination thereof. The depolymerization catalyst can achieve depolymerization of the polyolefin waste feed, but the catalyst may also carry out additional reactions. For example, the depolymerization catalyst may achieve dehydrogenation, hydrogenolysis, cracking, isomerization, dehydrohalogenation, dehalogenation, or a combination thereof, of the process feed.

In one aspect, the depolymerization catalyst can comprise, consist essentially of, or be a zeolite-based catalyst. The zeolite-based catalyst can comprise any zeolite. For example, in aspects, the zeolite-based catalyst can comprise, consist essentially of, or be L-Zeolite (Zeolite L or LTL), X-Zeolite (Zeolite X), Y-Zeolite (Zeolite Y), omega Zeolite, beta Zeolite, SAPO-34 Zeolite, USY Zeolite, HY Zeolite, ZSM-4, ZSM-5 (MFI), ZSM-10, ZSM-11, ZSM-12, ZSM-20, ZSM-22, ZSM-23, ZSM-34, ZSM-35, ZSM-50, REY, USY, RE-USY, LZ-210, LZ-210-A, LZ-210-M, LZ-210-T, SSZ-13, SSZ-24, SSZ-26, SSZ-31, SSZ-33, SSZ-35, SSZ-37, SSZ-41, SSZ-42, SSZ-44, MCM-58, H-MOR (H-mordenite), mazzite, faujasite, chabazite, and the like, a modified mesoporous form thereof, an acid-modified form thereof, or any combination thereof. In an aspect, the zeolite of the zeolite-based catalyst can include unbound or bound zeolites in which the zeolite can have an effective pore diameter of about 7 angstroms or larger.

The zeolite-based catalyst can comprise any zeolite and can further comprise a binder for the zeolite. The zeolite binder can comprise, can consist essentially of, or can be any inorganic oxide, including but not limited to silica, alumina, clays, titania, magnesium oxide, and combinations thereof. In an aspect, the zeolite-based catalyst with a silica binder can be prepared from a silica sol. In another aspect, the zeolite-based catalyst with an alumina binder can be prepare from a solution. The resulting pastes from these mixtures can be fired to make the bound zeolite-based catalysts. In one aspect, the zeolite-based catalyst can include the zeolite or combination of zeolites and any amount of binder that can provide the zeolite-based catalyst in a suitable solid structure after processing. For example, the zeolite-based catalyst can include the zeolite or combinations of zeolites and from about 15 wt % to about 35 wt % binder, alternatively from about 20 wt % to about 30 wt % binder, or alternatively any weight percentage between these values.

In another aspect, associated with the zeolites are certain transition metals to affect the catalytic depolymerization. For example, the zeolite-based catalyst can comprise chromium, molybdenum, tungsten, iron, ruthenium, osmium, cobalt, rhodium, iridium, nickel, palladium, platinum, zinc, magnesium, gallium, titanium, tantalum, or any combination thereof. In one aspect, the zeolite-based catalyst can comprise one or more of the platinum metals. In another aspect, the zeolite-based catalyst comprises rhodium, iridium, palladium, platinum, ruthenium, osmium, or a combination thereof. In embodiments, the zeolite-based catalyst can comprise or can be selected from Pt-L-Zeolite, Pt-ZSM-5, Pt—Y zeolite, Pt-SAPO-34 zeolite, Pt-USY zeolite, Pt-HY zeolite, Pt-beta zeolite, or any combination thereof.

In other embodiments, the zeolite-based catalyst can comprise fluorine, chlorine, bromine, iodine, or any combination thereof. In an aspect, the transition metal-zeolite catalysts such as Pt-L-Zeolite, Pt-ZSM-5, Pt—Y zeolite, Pt-SAPO-34 zeolite, Pt-USY zeolite, Pt-HY zeolite, and Pt-beta zeolite, can include halide content, such as chloride or fluoride content, which can be beneficial to the activity and longevity of the zeolite-based catalysts. Both fluoride concentrations and chloride concentrations can enhance the performance of the zeolite-based catalyst. In an aspect, for example, the chloride concentration in the zeolite-based catalyst can be from about 0.1 wt. % to about 4.0 wt. % or from about 0.5 wt. % to about 3.5 wt. %. In another aspect, the fluoride concentration in the zeolite-based catalyst of from about 0.1 wt. % to about 5.0 wt. % or from about 0.5 wt. % to about 4.0 wt. %. These halide weight concentrations are recited based on the dry weight of the calcined zeolite-based catalyst prior to reduction.

In the chloride-containing zeolite-based catalysts, the catalyst can comprise up to about 5.0 wt. %, up to about 4.0 wt. %, up to about 3.5 wt. %, up to about 3.0 wt. %, or up to about 2.5 wt. % chloride, in which these concentrations are based on the dry weight of the calcined zeolite-based catalyst prior to reduction. In the fluoride-containing catalysts, the catalyst can comprise up to about 5.0 wt. %, up to about 4.0 wt. %, up to about 3.5 wt. %, up to about 3.0 wt. %, or up to about 2.5 wt. % fluoride relative to the dry weight of the calcined zeolite-based catalyst prior to reduction.

In a further aspect, the zeolite-based depolymerization catalyst can further comprise a promoter selected from a Group 1, 2, 14 or 15 metal. In particular, the zeolite-based catalyst can further comprise a promoter selected from tin, bismuth, or a combination thereof. When the promoter comprises tin, the tin content can be imparted by treating the zeolite or the zeolite-based depolymerization catalyst itself with a tin salt or compound, such as stannous chloride, stannic chloride, stannic tartrate, stannic nitrate, and the like.

In a further aspect of this disclosure, the step of contacting the process feed with the zeolite-based catalyst to form a reactor effluent can further comprise contacting the process feed in the depolymerization reactor with a non-zeolite cracking catalyst. In this aspect, a non-zeolite cracking catalyst can comprise or can be selected from clays, acid treated clays, perovskites, layered titanates, silica alumina, silica-coated alumina, acidic alumina, tungstated zirconia, activated carbon, natural kaolin, acid-modified kaolin, bentonite, and the like.

The zeolite-based catalyst used according to this disclosure can be characterized by a suitable pore volume of the zeolite itself, examples of which are about 0.10 mL/g, about 0.25 mL/g, about 0.50 mL/g, about 0.75 mL/g, about 1.0 mL/g, about 1.25 mL/g, about 1.50 mL/g, about 1.75 mL/g, about 2.0 mL/g, or any range between any of these zeolite pore volumes. In some aspects the zeolite-based catalyst is characterized zeolite pore volumes of from about 0.10 mL/g to about 2.0 mL/g, from about 0.25 mL/g to about 1.75 mL/g, or from about 0.50 mL/g to about 1.50 mL/g. These quantitative pore volumes are features of the starting zeolite itself prior to forming the catalyst using the transition metals and promoters as described herein.

The zeolite pore diameters of the zeolite-based catalysts can vary. In an aspect, the zeolite-based catalyst can be characterized by a zeolite pore diameter of from about 4.0 Å (0.4 nm) to about 10 Å (1 nm), from about 5.0 Å (0.5 nm) to about 9.0 Å (0.9 nm), or from about 5.5 Å (0.55 nm) to about 7.0 Å (0.7 nm). In a further aspect, the zeolite-based catalyst is characterized by a pore diameter of from about 7 Å (0.7 nm) to about 10 Å (1 nm), from about 5 Å (0.5 nm) to about 6 Å (0.6 nm), or from about 2 Å (0.2 nm) to about 3 Å (0.3 nm). These quantitative pore diameters are features of the starting zeolite itself prior to forming the catalyst using the transition metals and promoters as described herein.

The zeolite-based catalyst can also be characterized by a catalyst surface area of about 100 $m^2/g$, about 200 $m^2/g$, about 300 $m^2/g$, about 400 $m^2/g$, about 500 $m^2/g$, about 600 $m^2/g$, about 700 $m^2/g$, about 800 $m^2/g$, about 900 $m^2/g$, about 1,000 $m^2/g$, or any range between any of these surface areas. In some aspects, the zeolite-based catalyst is characterized a catalyst surface area of from about 100 $m^2/g$ to about 1,000 $m^2/g$, from about 200 $m^2/g$ to about 1,000 $m^2/g$, or from about 200 $m^2/g$ to about 900 $m^2/g$.

In embodiments, the zeolite-based catalyst is in particulate form and can have an average particle size of from about 2 μm to about 300 μm, from about 3 μm to about 200 μm, from about 4 μm to about 100 μm, or from about 5 μm to about 25 μm. For example, the zeolite-based catalyst can comprise Y-zeolite and can be in particulate form having an average particle size of from about 3 μm to about 8 μm. The zeolite-based catalyst may also comprise ZSM-5 zeolite and can be in particulate form having an average particle size of from about 5 μm to about 10 μm. In another aspect, the zeolite-based catalyst can comprise H-MOR and can be in particulate form having an average particle size of from about 12 μm to about 18 μm. The zeolite-based catalyst also may comprise beta Zeolite and can be in particulate form having an average particle size of from about 3 μm to about 5 μm.

According to a further aspect, the process feed can be contacted under depolymerization conditions with a non-zeolite cracking catalyst before, after, or during the step of providing the reactor feed to a second heating zone. For example, the process for converting plastic waste can further comprise contacting the process feed in the depolymerization reactor with a non-zeolite cracking catalyst comprising or selected from clays, acid treated clays, perovskites, layered titanates, silica alumina, silica-coated alumina, acidic alumina, tungstated zirconia, activated carbon, natural kaolin, acid-modified kaolin, bentonite, or any combination thereof.

In another aspect, the depolymerization catalyst can comprise, consist essentially of, or be a chromia-based catalyst, or chromia-based catalyst in combination with zeolite-based catalyst. For example, the chromia-based catalyst may comprise a chromium oxide such as amorphous $Cr_2O_3$ or crystalline $Cr_2O_3$. The chromia-based catalyst may be supported on silica, silica-alumina, silica-coated alumina, silica-titania, silica-magnesia, alumina, zirconia, thoria, mixed oxides thereof, or mixtures thereof. For example, the chromia-based catalyst can comprise: chromia-alumina; chromia-magnesia-alumina; magnesium chromite-tin oxide; magnesium chromite-alumina-tin oxide; magnesium chromite combined with a promoter selected from B, Si, Sn, Pb, Zn, or Se; or any combination thereof. The B, Si, Sn, Pb, Zn, or Se promoter can be present from 0.1 wt. % to 10 wt. % relative to the combined chromia (on a $Cr_2O_3$ basis) and the promoter.

Chemically-Modified Solid Oxide (SSA)

In a further aspect, it has been found that contacting the process feed, the hydrocarbon co-feed, or the reactor feed with a chemically-modified solid oxide which comprises a solid oxide treated with an electron-withdrawing anion and which is referred to as a solid super-acid or "SSA", during one or more stages in the process of converting plastic waste can provide improvements in the process. In an aspect, the SSA can provide substantial acidity such as Lewis acidity during the process steps. For example, a solid super-acid can be used during the step of heating the process feed in the presence or absence of the hydrocarbon co-feed, or the step of contacting the reactor feed with the depolymerization catalyst such as a zeolite-based catalyst. While not intending to be bound by theory, it is thought that the presence of the SSA may start the process of degrading the polyolefins into shorter polymer or oligomer chains sooner, which can enhance the depolymerization reaction in the presence of the zeolite-based or other depolymerization catalyst.

The solid super-acid may be used advantageously at any stage of the process for converting plastic waste. For example, the process feed comprising the polyolefin waste can be contacted with an SSA in the first heating zone in the presence or in the absence of the hydrocarbon co-feed. In another aspect, the reactor feed can be contacted with an SSA before it enters the second heating zone, or within the second heating zone in the depolymerization reactor. In a further aspect, the SSA can be used in both the first heating zone and in the second heating zone. For example, in one aspect, provided herein is a process for converting plastic waste, the process comprising:
  (a) providing a process feed comprising a polyolefin waste to a first heating zone and heating the process feed in the presence of a chemically-modified solid oxide comprising a solid oxide treated with an electron-withdrawing anion;
  (b) combining a hydrocarbon co-feed with the process feed to form a reactor feed;
  (c) providing the reactor feed to a second heating zone and heating the reactor feed in the presence of a depolymerization catalyst under depolymerization conditions to form a reactor effluent; and
  (d) separating the reactor effluent into a plurality of output streams, each output stream comprising a circular product.

In one aspect, the depolymerization catalyst such as a zeolite-based catalyst can be used with a chemically-modified solid oxide, that is, when the reactor feed is contacted with the depolymerization catalyst under depolymerization conditions in the second heating zone to form a reactor effluent. The chemically-modified solid oxide can be generated by treatment of a solid oxide with an acid of an electron-withdrawing anion or a salt of an electron-withdrawing anion. Following this treatment of the solid oxide with the acid or the salt of an electron-withdrawing anion, the chemically-modified solid oxide can be dried and calcined to provide the active chemically-modified solid oxide or SSA.

In embodiments, the solid oxide of the chemically-modified solid oxide can comprise or can be selected from $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof (for example, silica-alumina), and any combinations thereof. For example, the chemically-modified solid oxide can comprise a solid oxide comprising or selected from silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

In a further aspect, the chemically-modified solid oxide comprises a solid oxide that is chemically modified with an electron-withdrawing anion, wherein the electron-withdrawing anion comprises or is selected from sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof. For example, the chemically-modified solid oxide can be generated by treatment of a solid oxide with sulfuric acid, sulfate ion, bisulfate ion, fluoro sulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

Therefore, in an aspect, the chemically-modified solid oxide can comprise a sulfur oxoacid anion-modified solid oxide, a phosphorus oxoacid anion-modified solid oxide, or a halide ion-modified solid oxide. For example, the chemically-modified solid oxide can comprise a sulfated solid oxide, bisulfated (hydrogen sulfated) solid oxide, fluoro sulfated solid oxide, phosphated solid oxide, fluorophosphated solid oxide, fluorided solid oxide, or chlorided solid oxide.

In further aspects, the chemically-modified solid oxide can comprise a solid oxide that is chemically modified with an electron-withdrawing anion, wherein:
  the solid oxide can comprise or be selected from silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and
  the electron-withdrawing anion can comprise or be selected from sulfate, bisulfate, fluorosulfate, phosphate, fluorophosphates, fluoride, or chloride.

For example, the chemically-modified solid oxide can comprise sulfated alumina, sulfated silica-alumina, or sulfated silica-coated alumina.

According to another aspect, the chemically-modified solid oxide itself can be metal-treated with a metal cation selected from a Group 1, 2, 12, or 13 metal.

Output Streams and Circular Products

Once the reactor feed and the depolymerization catalyst are contacted in the depolymerization zone under depolymerization conditions to form a reactor effluent, the reactor effluent can be provided to a separation unit to separate the reactor effluent into a plurality of output streams, each output stream comprising at least one circular product. By describing a reactor effluent, it is intended to reflect that there may be more than one reactor effluent from the second heating zone which can be further separated. For example, the reactor effluent from the second heating zone in the depolymerization reactor can include a liquid effluent and also can include a gaseous effluent which may be discharged from an overhead outlet of the depolymerization reactor. For example, the gaseous effluent can comprise a $C_2$-$C_5$ hydrocarbon effluent.

In an aspect, the plurality of output streams can comprise a light hydrocarbon stream, a medium hydrocarbon stream, a heavy hydrocarbon stream, or any combination thereof. In another aspect, one of the plurality of output streams can comprise $C_2$-$C_5$ saturated hydrocarbons, and this stream can further comprise $C_2$-$C_5$ unsaturated hydrocarbons. One of the plurality of output streams can comprise $C_6$-$C_8$ saturated hydrocarbons, and this output stream can further comprise $C_6$-$C_8$ unsaturated hydrocarbons. Another of the plurality of output streams can comprise $C_{9+}$ hydrocarbons. In embodiments, the plurality of output streams can comprise a $C_2$-$C_5$ hydrocarbon stream, a $C_6$-$C_8$ hydrocarbon stream, and a heavy ($C_{9+}$) hydrocarbon stream.

Depending upon the nature of the process feed and a hydrocarbon co-feed, the reactor feed can include halogen-containing materials. Therefore, any of the output streams can comprise halogenated hydrocarbons, and the process for converting plastic waste can further comprise the step of dehydrohalogenation of the halogenated hydrocarbons. For example, one output stream can comprise $C_2$-$C_5$ hydrocarbons and halogenated hydrocarbons, and the process for converting plastic waste can further comprise the step of dehydrohalogenation of the halogenated hydrocarbons. In an aspect, one output stream can comprise $C_6$-$C_8$ hydrocarbons and halogenated hydrocarbons, and the process for converting plastic waste can further comprises the step of dehydrohalogenation of the halogenated hydrocarbons.

In other aspects of this process, one output stream can comprise $C_2$-$C_5$ hydrocarbons, and the process for converting plastic waste can further comprise the step of providing the $C_2$-$C_5$ hydrocarbons to a steam cracker to produce a stream cracker effluent comprising circular ethylene and/or circular propylene. One output stream also may comprise $C_6$-$C_8$ hydrocarbons, and the process for converting plastic waste can further comprise the step of providing the $C_6$-$C_8$ hydrocarbons to a reforming unit or an AROMAX® unit to produce one or more circular aromatic products. One output stream also may comprise $C_6$-$C_8$ hydrocarbons, and the process for converting plastic waste can further comprise the step of providing the $C_6$-$C_8$ hydrocarbons to a steam cracker to produce a stream cracker effluent comprising circular ethylene and/or circular propylene.

Depolymerization System

In addition to depolymerization processes, this disclosure provides depolymerization systems for converting plastics including plastic wastes to hydrocarbons, specifically liquid and gaseous depolymerization reactor products, which subsequently can be used as feeds or co-feeds for making circular products.

In an aspect, there is provided a system for converting plastic waste, the system comprising:
(a) a first heating zone configured to receive a process feed and optionally receive a first hydrocarbon co-feed, and heat the process feed to provide a reactor feed;
(b) a depolymerization reactor comprising a first feed inlet configured to receive the reactor feed, a second heating zone, and at least one outlet configured to discharge a reactor effluent, and configured to contact the reactor feed with a depolymerization catalyst under depolymerization conditions; and
(c) a separation unit, configured to receive and separate the reactor effluent into a plurality of output streams, each output stream comprising a circular product.

The reactor effluent from the depolymerization reactor can include a liquid effluent and also can include a gaseous effluent which may be discharged overhead from the depolymerization reactor. The plurality of output streams can comprise, for example, a light hydrocarbon stream ($C_2$-$C_5$), a medium hydrocarbon stream ($C_6$-$C_8$), a heavy hydrocarbon stream ($C_{9+}$), or any combination thereof.

In an aspect, the first heating zone is not limited to any particular heating unit. For example, the first heating zone can comprise an extruder. The first heating zone also can include mixer configured to mix the process feed and the hydrocarbon co-feed as it is being heated to form the reactor feed.

In another aspect, the depolymerization reactor can comprises a second feed inlet configured to receive a second hydrocarbon co-feed. The second hydrocarbon co-feed can be the same or different from the first hydrocarbon co-feed. The depolymerization reactor can comprise a first outlet configured to discharge a gaseous reactor effluent and a second outlet configured to discharge a liquid reactor effluent.

The separation unit in the system for converting plastic waste can comprise one or more condensers downstream of the depolymerization unit, which are configured to separate the reactor effluent into the plurality of output streams. For example, the plurality of output streams comprise a light hydrocarbon stream, a medium hydrocarbon stream, a heavy hydrocarbon stream, or any combination thereof. In an aspect, the separation unit can be configured to separate the reactor effluent into a light hydrocarbon stream comprising $C_2$-$C_5$ hydrocarbons, a medium hydrocarbon stream comprising $C_6$-$C_8$ hydrocarbons, and a heavy hydrocarbon stream comprising $C_{9+}$ hydrocarbons.

In embodiments, the plurality of output streams in the system for converting plastic waste can include a $C_2$-$C_5$ hydrocarbon stream, and the system can further comprise a steam cracker configured to receive the $C_2$-$C_5$ hydrocarbon stream and produce a stream cracker effluent comprising circular ethylene and/or circular propylene. The plurality of output streams also can include a $C_6$-$C_8$ hydrocarbon stream, and the system can further comprise a steam cracker configured to receive the $C_6$-$C_8$ hydrocarbon stream and produce a stream cracker effluent comprising circular ethylene and/or circular propylene.

In embodiments, the plurality of output streams in the system for converting plastic waste also may include a $C_6$-$C_8$ hydrocarbon stream, and the system may further comprise an AROMAX® unit or a reforming unit configured to receive the $C_6$-$C_8$ hydrocarbon stream and produce one or more circular aromatic products.

In other embodiments, the plurality of output streams in the system for converting plastic waste can include a $C_9$ and heavier ($C_{9+}$) hydrocarbon stream, and the system can further comprise a fluid catalytic cracker (FCC) configured to receive the $C_{9+}$ stream and produce an FCC effluent comprising circular naphtha ($C_6$-$C_{10}$ hydrocarbons) and circular $C_5$ and lighter ($C_{5-}$) hydrocarbons. If desired or needed for downstream processes, the system for converting plastic waste can further comprise a pretreater between the separation unit and a fluid catalytic cracker (FCC) configured to receive the $C_{9+}$ stream and form a treated $C_{9+}$ stream having a lower sulfur, halogen, or aromatic content as compared with the $C_{9+}$ stream prior to pretreating.

According to an aspect, one of the plurality of output streams is a heavy hydrocarbon stream, and the system can further comprise a recycle pump and recycle line from the separation unit to the depolymerization reactor configured to return at least a portion of the heavy hydrocarbon stream from the separation unit to the depolymerization reactor. This configuration boosts the yields of the light and medium hydrocarbons and therefore, the yields of any downstream circular products produced from the light and medium hydrocarbons.

In one aspect, the system for converting plastic waste can further comprise a dehydrohalogenation unit downstream of the separation unit which is configured to receive any one of the plurality of output streams and reduce the halogen concentration therein. In particular, any of the $C_2$-$C_5$ hydrocarbon output stream, the $C_6$-$C_8$ hydrocarbon output stream, or the $C_{9+}$ hydrocarbon output stream can further comprise halogenated hydrocarbons. For example, one output stream may comprise $C_2$-$C_5$ hydrocarbons and halogenated hydrocarbons, and the system can further comprise a dehydrohalogenation unit between the separation unit and the steam cracker. In another embodiment, one output stream may comprise $C_6$-$C_8$ hydrocarbons and halogenated hydrocarbons, and the system can further comprise a dehydrohalogenation unit between the separation unit and the steam cracker, the AROMAX® unit, or the reforming unit. In a further embodiment, the output stream may comprise $C_{9+}$ hydrocarbons and halogenated hydrocarbons, and the system can further comprise a dehydrohalogenation unit between the separation unit and the fluid catalytic cracker or between the separation unit and the depolymerization reactor in the recycle line.

In a further aspect, the depolymerization reactor may further comprise a second feed inlet configured to receive a second hydrocarbon co-feed. The second hydrocarbon co-feed can then contact the depolymerization catalyst under depolymerization conditions along with reactor feed which is received into the depolymerization reactor through the first feed inlet. The second hydrocarbon co-feed may be used for any number of reasons, for example, when feeding a different second hydrocarbon co-feed when it is desirable to not combine the second hydrocarbon co-feed with the process feed to provide the reactor feed. In this case the second hydrocarbon co-feed can comprise or can be selected independently from a pyrolysis oil, a pyrolysis oil fraction, a petroleum-based co-feed, a fossil fuel-based co-feed, or a bio-based co-feed. For example, the second hydrocarbon co-feed can comprise or can be selected from a pyrolysis oil, a pyrolysis oil fraction, a $C_5$-$C_6$ saturated hydrocarbon, natural gas liquids (NGL), light naphtha, heavy naphtha, or combinations thereof. When the second hydrocarbon co-feed can comprise a pyrolysis oil, the pyrolysis oil can be derived from any of the polymer materials that are used to generate the hydrocarbon co-feed, and the second hydrocarbon co-feed can include a natural or a synthetic antioxidant if desired, for example, the same of different antioxidants that can be used in the hydrocarbon co-feed.

FIG. 1 illustrates aspects of the disclosure showing an exemplary embodiment of a depolymerization reactor system and process for the production of circular products. Illustrated in FIG. 1 are depolymerization system 10 for converting plastic waste, which includes a first heating zone 15, which is adapted to receive a process feed 20 and a hydrocarbon co-feed 25 and heat them in the first heating zone to produce a liquid reactor feed 30. Liquid reactor feed 30 is fed to the depolymerization reactor 35 which is configured to receive the liquid reactor feed through a first feed inlet, contact the liquid reactor feed with the zeolite-based depolymerization catalyst under depolymerization conditions, and discharge a reactor effluent 40. Downstream of depolymerization reactor 30 is separation unit 45 which is adapted to separate the reactor effluent into a plurality of output streams, each output stream comprising a circular product. In the FIG. 1 embodiment, the separation unit 45 is shown to separate reactor effluent 40 into a light ($C_2$-$C_5$) output stream 50, a medium ($C_6$-$C_8$) output stream 55, and a heavy ($C_{9+}$) output stream 60. As illustrated, this process and system can further include the option of recycling at least a portion of the heavy fraction from the separation unit to the depolymerization reactor.

The FIG. 1 embodiment also illustrates an optional dehydrohalogenation (or "dehalogenation") unit 65 is downstream of the separation unit 45 which is configured to receive the light ($C_2$-$C_5$) output stream 50 and reduce the concentration of or remove halogenated components. In this embodiment, the dehalogenated light output stream is fed to a steam cracker 70 to produce a stream cracker effluent comprising circular ethylene and/or circular propylene. Also illustrated are an AROMAX® unit or reforming unit 75 adapted to receive medium ($C_6$-$C_8$) output stream 55 from separation unit 45 and produce one or more circular aromatic products. The medium ($C_6$-$C_8$) output stream 55 can also be fed to steam cracker 70 to produce a stream cracker effluent comprising circular ethylene and/or circular propylene.

Also illustrated in the FIG. 1 embodiment is heavy ($C_{9+}$) output stream 60 which can be fed to fluid catalytic cracker (FCC) 80 to produce a lighter hydrocarbon stream for further use. If desired, at least a portion of heavy ($C_{9+}$) output stream 60 can be recycled to the depolymerization reactor 35 by way of recycle line 85, to improve the yields of the light and medium hydrocarbons and any downstream circular products produced therefrom.

This FIG. 1 embodiment also illustrates an overhead take off from the depolymerization reactor which can transport overhead reactor effluent 90 to steam cracker 70, optionally through optional dehydrohalogenation (or "dehalogenation") unit 65 is downstream of the separation unit 45. Thus, reference to the reactor effluent include any reactor effluent discharged from the depolymerization unit through any one of more outlets.

ASPECTS OF THE DISCLOSURE

The invention is described above with reference to numerous aspects, embodiments, and specific examples. Many variations will suggest themselves to those skilled in the art in light of the above detailed description. All such obvious variations are within the full intended scope of the appended claims. Other aspects of the invention can include, but are not limited to, the following. Aspects which are described as "comprising" certain components or steps, may also "consist essentially of" or "consist of" those components or steps, unless stated otherwise.

Aspect 1. A process for converting plastic waste, the process comprising:
(a) providing a process feed comprising a polyolefin waste to a first heating zone and heating the process feed;
(b) combining a hydrocarbon co-feed with the process feed to form a reactor feed;
(c) providing the reactor feed to a second heating zone and heating the reactor feed in the presence of a depolymerization catalyst under depolymerization conditions to form a reactor effluent; and
(d) separating the reactor effluent into a plurality of output streams, each output stream comprising a circular product.

Aspect 2. The process for converting plastic waste according to Aspect 1, wherein combining the hydrocarbon co-feed with the process feed occurs before, during, or after heating the process feed, or any combination thereof.

Aspect 3. The process for converting plastic waste according to any of the preceding Aspects, wherein the process feed is a solid at 25° C.

Aspect 4. The process for converting plastic waste according to any of the preceding Aspects, wherein the hydrocarbon co-feed is a liquid or a solid (e.g., a wax) at 25° C.

Aspect 5. The process for converting plastic waste according to any of the preceding Aspects, wherein the reactor feed provided to the second heating zone is liquid.

Aspect 6. The process for converting plastic waste according to any of the preceding Aspects, wherein heating the process feed in the first heating zone melts the polyolefin waste.

Aspect 7. The process for converting plastic waste according to any of the preceding Aspects, wherein the first heating zone comprises an extruder.

Aspect 8. The process for converting plastic waste according to any of the preceding Aspects, wherein combining the hydrocarbon co-feed with the process feed occurs before, during, or after providing the process feed to the first heating zone.

Aspect 9. The process for converting plastic waste according to any of the preceding Aspects, further comprising combining the depolymerization catalyst with the process feed in the first heating zone.

Aspect 10. The process for converting plastic waste according to any of the preceding Aspects, further comprising combining the depolymerization catalyst with the reactor feed before or after providing the reactor feed to the second heating zone.

Aspect 11. The process for converting plastic waste according to any of the preceding Aspects, wherein the reactor effluent comprises a gaseous reactor effluent and a liquid reactor effluent.

Aspect 12. The process for converting plastic waste according to any of the preceding Aspects, further comprising introducing additional process feed into the second heating zone under depolymerization conditions.

Aspect 13. The process for converting plastic waste according to any of the preceding Aspects, further comprising introducing additional hydrocarbon co-feed into the second heating zone under depolymerization conditions.

Aspect 14. The process for converting plastic waste according to any of the preceding Aspects, wherein one of the output streams is recycled to the second heating zone.

Aspect 15. The process for converting plastic waste according to any of the preceding Aspects, wherein the second heating zone comprises a fixed bed reactor or a fluidized bed reactor.

Aspect 16. The process for converting plastic waste according to any of the preceding Aspects, wherein the process feed further comprises additional plastic waste which is different from the polyolefin waste.

Aspect 17. The process for converting plastic waste according to any of the preceding Aspects, wherein the amount or the fraction of the circular product attributable to the polyolefin waste or the additional plastic waste in one or more output streams is determined by mass balance.

Aspect 18. The process for converting plastic waste according to any of the preceding Aspects, wherein the process further comprises certifying the circular product attributable to the polyolefin waste or the additional plastic waste in one or more output streams as Circular in accordance with International Sustainability and Carbon Certification (ISCC) standards, based upon the amount or the fraction of the circular product attributable to the polyolefin waste or the additional plastic waste in one or more output streams determined by mass balance and the free attribution method.

Aspect 19. The process for converting plastic waste according to any of the preceding Aspects, wherein the process feed is heated in the first heating zone to a temperature that is 15° F. (8° C.) to 50° F. (28° C.) below the boiling temperature of the hydrocarbon co-feed.

Aspect 20. The process for converting plastic waste according to any of the preceding Aspects, wherein the process feed is heated in the first heating zone to a temperature of from 150° F. (66° C.) to 350° F. (177° C.), or to a temperature that is 15° F. (8° C.) to 50° F. (28° C.) below the boiling temperature of the hydrocarbon co-feed.

Aspect 21. The process for converting plastic waste according to any of the preceding Aspects, wherein the process feed is heated in the first heating zone to a temperature of about 150° F. (66° C.), about 160° F. (71° C.), about 170° F. (77° C.), about 180° F. (82° C.), about 190° F. (88° C.), about 200° F. (93° C.), about 210° F. (99° C.), about 220° F. (104° C.), about 230° F. (110° C.), about 240° F. (116° C.), about 250° F. (121° C.), about 260° F. (127° C.), about 270° F. (132° C.), about 280° F. (138° C.), about 290° F. (143° C.), about 300° F. (149° C.), about 310° F. (154° C.), about 320° F. (160° C.), about 330° F. (166° C.), about 340° F. (171° C.), or about 350° F. (177° C.).

Aspect 22. The process for converting plastic waste according to any of the preceding Aspects, wherein the depolymerization conditions comprise heating the reactor feed and the depolymerization catalyst in the second heating zone at a temperature for a time period sufficient to depolymerize at least a portion of the polyolefin waste.

Aspect 23. The process for converting plastic waste according to any of the preceding Aspects, wherein the depolymerization conditions comprise heating the reactor feed and the depolymerization catalyst in the second heating zone to a temperature of from 300° F. (149° C.) to 1,000° F. (538° C.), from 400° F. (204° C.) to 900° F. (482° C.), or from 450° F. (232° C.) to 800° F. (427° C.).

Aspect 24. The process for converting plastic waste according to any of the preceding Aspects, wherein the depolymerization conditions comprise heating the reactor feed and the depolymerization catalyst in the second heating zone to a temperature of about 300° F. (149° C.), about 350° F. (177° C.), about 400° F. (204° C.), about 450° F. (232° C.), about 500° F. (260° C.), about 550° F. (188° C.), about 600° F. (316° C.), about 650° F. (343° C.), about 700° F. (371° C.), about 750° F. (399° C.), about 800° F. (427° C.), about 850° F. (454° C.), about 900° F. (482° C.), about 950° F. (510° C.), about 1000° F. (538° C.), or any range between any of these temperatures, while contacting the reactor feed and the depolymerization catalyst.

Aspect 25. The process for converting plastic waste according to any of the preceding Aspects, wherein depolymerization conditions comprise heating the reactor feed and the depolymerization catalyst in the second heating zone in the presence of hydrogen.

Aspect 26. The process for converting plastic waste according to any of the preceding Aspects, wherein depolymerization conditions comprise heating the reactor feed and the depolymerization catalyst in the second heating zone in the presence of hydrogen at a pressure of from about 5 psig (34 kPa) to about 1,000 psig (6895 kPa).

Aspect 27. The process for converting plastic waste according to any of the preceding Aspects, wherein depolymerization conditions comprise heating the reactor feed and the depolymerization catalyst in the second heating zone in the presence of hydrogen at a pressure of about 5 psig (34 kPa), about 25 psig (172 kPa), about 50 psig (335 kPa), about 100 psig (689 kPa), about 150 psig (1034 kPa), about 200 psig (1379 kPa), about 250 psig (1724 kPa), about 300 psig (2068 kPa), about 350 psig (2413 kPa), about 400 psig (2758 kPa), about 450 psig (3103 kPa), about 500 psig (3447 kPa), about 550 psig (3792 kPa), about 600 psig (4137 kPa), about 650 psig (4482 kPa), about 700 psig (4826 kPa), about 750 psig (5171 kPa), about 800 psig (5516 kPa), about 850 psig (5861 kPa), about 900 psig (6205 kPa), about 950 psig (6550 kPa), about 1000 psig (6895 kPa), or any range between any of these pressures.

Aspect 28. The process for converting plastic waste according to any of Aspects 1-24, wherein depolymerization conditions comprise heating the reactor feed and the depolymerization catalyst in the second heating zone in the absence of hydrogen.

Aspect 29. The process for converting plastic waste according to any of the preceding Aspects, wherein the depolymerization catalyst comprises a zeolite-based catalyst, a chromia-based catalyst, or a combination thereof.

Aspect 30. The process for converting plastic waste according to Aspect 29, wherein the zeolite-based catalyst, the chromia-based catalyst, or the combination thereof achieves dehydrogenation, hydrogenolysis, cracking, isomerization, dehydrohalogenation, dehalogenation, or a combination thereof, of the reactor feed.

Aspect 31. The process for converting plastic waste according to any of Aspects 29-30, wherein the zeolite-based catalyst comprises any zeolite.

Aspect 32. The process for converting plastic waste according to any of Aspects 29-31, wherein the zeolite-based catalyst comprises L-Zeolite (Zeolite L or LTL), X-Zeolite (Zeolite X), Y-Zeolite (Zeolite Y), omega Zeolite, beta Zeolite, SAPO-34 Zeolite, USY Zeolite, HY Zeolite, ZSM-4, ZSM-5 (MFI), ZSM-10, ZSM-11, ZSM-12, ZSM-20, ZSM-22, ZSM-23, ZSM-34, ZSM-35, ZSM-50, REY, USY, RE-USY, LZ-210, LZ-210-A, LZ-210-M, LZ-210-T, SSZ-13, SSZ-24, SSZ-26, SSZ-31, SSZ-33, SSZ-35, SSZ-37, SSZ-41, SSZ-42, SSZ-44, MCM-58, H-MOR (H-mordenite), mazzite, faujasite, chabazite, a modified mesoporous form thereof, an acid-modified form thereof, or any combination thereof.

Aspect 33. The process for converting plastic waste according to any of Aspects 29-32, wherein the zeolite-based catalyst comprises chromium, molybdenum, tungsten, iron, ruthenium, osmium, cobalt, rhodium, iridium, nickel, palladium, platinum, zinc, magnesium, gallium, titanium, tantalum, or any combination thereof.

Aspect 34. The process for converting plastic waste according to any of Aspects 29-33, wherein the zeolite-based catalyst comprises Pt-L-Zeolite, Pt-ZSM-5, Pt—Y zeolite, Pt-SAPO-34 zeolite, Pt-SSZ-13 zeolite, Pt-USY zeolite, Pt-HY zeolite, Pt-beta zeolite, or any combination thereof.

Aspect 35. The process for converting plastic waste according to any of Aspects 29-34, wherein the zeolite-based catalyst comprises fluorine, chlorine, bromine, iodine, or any combination thereof.

Aspect 36. The process for converting plastic waste according to any of Aspects 29-35, wherein the zeolite-based catalyst comprises a chloride concentration of from about 0.1 wt. % to about 4.0 wt. % or from about 0.5 wt. % to about 3.5 wt. % relative to the dry weight of the calcined zeolite-based catalyst prior to reduction.

Aspect 37. The process for converting plastic waste according to any of Aspects 29-36, wherein the zeolite-based catalyst comprises a fluoride concentration of from about 0.1 wt. % to about 5.0 wt. % or from about 0.5 wt. % to about 4.0 wt. % relative to the dry weight of the calcined zeolite-based catalyst prior to reduction.

Aspect 38. The process for converting plastic waste according to any of Aspects 29-37, wherein the zeolite-based catalyst comprises a chloride concentration of up to about 5.0 wt. %, up to about 4.0 wt. %, up to about 3.5 wt. %, up to about 3.0 wt. %, or up to about 2.5 wt. % chloride relative to the dry weight of the calcined zeolite-based catalyst prior to reduction.

Aspect 39. The process for converting plastic waste according to any of Aspects 29-38, wherein the zeolite-based catalyst comprises a fluoride concentration of up to about 5.0 wt. %, up to about 4.0 wt. %, up to about 3.5 wt. %, up to about 3.0 wt. %, or up to about 2.5 wt. % fluoride relative to the dry weight of the calcined zeolite-based catalyst prior to reduction.

Aspect 40. The process for converting plastic waste according to any of Aspects 29-39, wherein the zeolite-based catalyst comprises a promoter selected from a Group 1, 2, 14 or 15 metal.

Aspect 41. The process for converting plastic waste according to any of Aspects 29-40, wherein the zeolite-based catalyst comprises a promoter selected from tin or bismuth.

Aspect 42. The process for converting plastic waste according to any of Aspects 29-41, wherein the zeolite-based catalyst is treated with a tin salt, e.g., stannous chloride, stannic chloride, stannic tartrate, or stannic nitrate.

Aspect 43. The process for converting plastic waste according to any of Aspects 29-42, wherein the zeolite of the zeolite-based catalyst is characterized by a zeolite pore volume of about 0.10 mL/g, about 0.25 mL/g, about 0.50 mL/g, about 0.75 mL/g, about 1.0 mL/g, about 1.25 mL/g, about 1.50 mL/g, about 1.75 mL/g, about 2.0 mL/g, or any range between any of these zeolite pore volumes.

Aspect 44. The process for converting plastic waste according to any of Aspects 29-43, wherein the zeolite of the zeolite-based catalyst is characterized by a zeolite pore diameter of from about 3.0 Å to about 10 Å, from about 4.0 Å to about 9.0 Å, from about 5.0 to about 8.0, or from about 5.5 Å to about 7.0 Å.

Aspect 45. The process for converting plastic waste according to any of Aspects 29-43, wherein the zeolite of the zeolite-based catalyst is characterized by a zeolite pore diameter of from about 7 Å (0.7 nm) to about 10 Å (1 nm), from about 5 Å (0.5 nm) to about 6 Å (0.6 nm), or from about 2 Å (0.2 nm) to about 3 Å (0.3 nm).

Aspect 46. The process for converting plastic waste according to any of Aspects 29-45, wherein the zeolite-based catalyst is characterized by a catalyst surface area of about 100 m$^2$/g, about 200 m$^2$/g, about 300 m$^2$/g, about 400 m$^2$/g, about 500 m$^2$/g, about 600 m$^2$/g, about 700 m$^2$/g, about 800 m$^2$/g, about 900 m$^2$/g, about 1,000 m$^2$/g, or any range between any of these surface areas.

Aspect 47. The process for converting plastic waste according to any of Aspects 29-46, wherein the zeolite-based catalyst is in particulate form having an average particle size of from about 2 μm to about 300 μm, from about 3 μm to about 200 μm, from about 4 μm to about 100 μm, from about 5 μm to about 200 μm, or from about 5 μm to about 25 μm.

Aspect 48. The process for converting plastic waste according to any of the preceding Aspects, wherein the zeolite-based catalyst comprises, consists essentially of, or is Y-zeolite and is in particulate form having an average particle size of from about 3 μm to about 8 μm.

Aspect 49. The process for converting plastic waste according to any of the preceding Aspects, wherein the zeolite-based catalyst comprises, consists essentially of, or is ZSM-5 (MFI) and is in particulate form having an average particle size of from about 5 μm to about 10 μm.

Aspect 50. The process for converting plastic waste according to any of the preceding Aspects, wherein the zeolite-based catalyst comprises, consists essentially of, or is H-MOR and is in particulate form having an average particle size of from about 12 μm to about 18 μm.

Aspect 51. The process for converting plastic waste according to any of the preceding Aspects, wherein the zeolite-based catalyst comprises, consists essentially of, or is beta Zeolite and is in particulate form having an average particle size of from about 3 μm to about 5 μm.

Aspect 52. The process for converting plastic waste according to any of the preceding Aspects, wherein the depolymerization catalyst comprises, consists essentially of, or is a chromia catalyst.

Aspect 53. The process for converting plastic waste according to Aspect 52, wherein the chromia-based catalyst comprises amorphous $Cr_2O_3$ or crystalline $Cr_2O_3$.

Aspect 54. The process for converting plastic waste according to any of Aspects 52-53, wherein the chromia-based catalyst supported on silica, silica-alumina, silica-coated alumina, silica-titania, silica-magnesia, alumina, zirconia, thoria, mixed oxides thereof, or mixtures thereof.

Aspect 55. The process for converting plastic waste according to any of Aspects 52-54, wherein the chromia-based catalyst comprises: chromia-alumina; chromia-magnesia-alumina; magnesium chromite-tin oxide; magnesium chromite-alumina-tin oxide; magnesium chromite combined with a promoter selected from B, Si, Sn, Pb, Zn, or Se; or any combination thereof.

Aspect 56. The process for converting plastic waste according to Aspect 55, wherein the promoter is present from 0.1 wt. % to 10 wt. % relative to the combined chromia (on a $Cr_2O_3$ basis) and the promoter.

Aspect 57. The process for converting plastic waste according to any of the preceding Aspects, further comprising contacting the reactor feed under depolymerization conditions with a non-zeolite cracking catalyst.

Aspect 58. The process for converting plastic waste according to any of the preceding Aspects, further comprising contacting the reactor feed under depolymerization conditions with a non-zeolite cracking catalyst comprising or selected from clays, acid treated clays, perovskites, layered titanates, silica alumina, silica-coated alumina, acidic alumina, tungstated zirconia, activated carbon, natural kaolin, acid-modified kaolin, bentonite, or any combination thereof.

Aspect 59. The process for converting plastic waste according to any of the preceding Aspects, wherein a halogen concentration in the reactor feed is controlled.

Aspect 60. The process for converting plastic waste according to any of the preceding Aspects, wherein a halogen concentration in the process feed, the hydrocarbon co-feed, or both the process feed and the hydrocarbon co-feed are controlled.

Aspect 61. The process for converting plastic waste according to any of the preceding Aspects, wherein a chlorine concentration or a fluorine concentration by weight in the reactor feed are, independently, less than 100 ppm, less than 90 ppm, less than 80 ppm, less than 70 ppm, less than 60 ppm, less than 50 ppm, less than 40 ppm, less than 30 ppm, less than 20 ppm, less than 10 ppm, or less than 5 ppm.

Aspect 62. The process for converting plastic waste according to any of the preceding Aspects, wherein the depolymerization catalyst comprises a zeolite-based catalyst and the halogen concentration in the process feed, the hydrocarbon co-feed, or the reactor feed are controlled to provide a halogen concentration in the zeolite-based catalyst of less than 10 wt. %, less than 7 wt. %, less than 5 wt. %, less than 4 wt. %, less than 3 wt. %, less than 2 wt. %, or less than less than 1 wt. %.

Aspect 63. The process for converting plastic waste according to any of the preceding Aspects, wherein the depolymerization catalyst comprises a zeolite-based catalyst and the chloride concentration in the process feed, the hydrocarbon co-feed, or the reactor feed are controlled to provide a chloride concentration in the zeolite-based catalyst of from 0.1 wt. % to 4.0 wt. %.

Aspect 64. The process for converting plastic waste according to any of the preceding Aspects, wherein the depolymerization catalyst comprises a zeolite-based catalyst and the fluoride concentration in the process feed, the hydrocarbon co-feed, or the reactor feed are controlled to provide a fluoride concentration in the zeolite-based catalyst of from 0.1 wt. % to 5.0 wt. %.

Aspect 65. The process for converting plastic waste according to any of the preceding Aspects, wherein the polyolefin waste comprises polyethylene, polypropylene, polystyrene, or any combination thereof.

Aspect 66. The process for converting plastic waste according to any of the preceding Aspects, wherein the polyolefin waste is present in the process feed or the reactor feed in a concentration of from greater than 0 wt. % or from 15 wt. % and up to 40 wt. %, 50 wt. %, 60 wt. %, 70 wt. %, or 80 wt. %.

Aspect 67. The process for converting plastic waste according to any of the preceding Aspects, wherein the polyolefin waste is present in the process feed or the reactor feed in a concentration of about 10 wt. %, about 20 wt. %, about 30 wt. %, about 40 wt. %, about 50 wt. %, about 60 wt. %, about 70 wt. %, about 80 wt. %, or any range between any of these weight percentages.

Aspect 68. The process for converting plastic waste according to any of the preceding Aspects, wherein the reactor feed further comprises a waste plastic other than the polyolefin waste.

Aspect 69. The process for converting plastic waste according to Aspect 68, wherein the waste plastic other than the polyolefin waste comprises polyester, polyamide, polyurethane, polyphenol, polycarbonate, polyvinyl halide, or any combination thereof.

Aspect 70. The process for converting plastic waste according to any of Aspects 68-69, wherein the waste plastic other than the polyolefin waste comprises polyethylene terephthalate (PET) or polyvinyl chloride (PVC).

Aspect 71. The process for converting plastic waste according to any of Aspects 68-70, wherein the waste plastic other than the polyolefin waste comprises polyvinyl chloride (PVC), and the polyvinyl chloride (PVC) is present in the reactor feed in a concentration of less than 10 wt. %, less than 5 wt. %, less than 2 wt. %, less than 1 wt. %, or less than 0.5 wt. %.

Aspect 72. The process for converting plastic waste according to any of the preceding Aspects, wherein the process feed is a solid characterized by an average particle size of less than or equal to 4 mm, less than or equal to 3 mm, less than or equal to 2 mm, less than or equal to 1 mm, or from about 1 mm to about 3 mm.

Aspect 73. The process for converting plastic waste according to any of the preceding Aspects, wherein the hydrocarbon co-feed comprises, consists essentially of, or is a petroleum-based co-feed, a fossil fuel-based co-feed, a bio-based co-feed, or any combination thereof.

Aspect 74. The process for converting plastic waste according to any of the preceding Aspects, wherein the hydrocarbon co-feed comprises, consists essentially of, or is a pyrolysis oil, a $C_5$-$C_6$ saturated hydrocarbon, natural gas liquids (NGL), light naphtha, heavy naphtha, or any combination thereof.

Aspect 75. The process for converting plastic waste according to any of the preceding Aspects, wherein the hydrocarbon co-feed comprises, consists essentially of, or is a pyrolysis oil, and wherein the pyrolysis oil is derived from pyrolysis of polyethylene, polypropylene, polystyrene, polyethylene terephthalate (PET), polyvinyl chloride (PVC), polyamide, polycarbonate, polyurethane, polyester, copolymers thereof, filled polymers thereof, composites thereof, natural or synthetic rubber, tires, or any combination thereof.

Aspect 76. The process for converting plastic waste according to any of the preceding Aspects, wherein a natural or a synthetic antioxidant is combined with the hydrocarbon co-feed or the reactor feed.

Aspect 77. The process for converting plastic waste according to Aspect 76, wherein the antioxidant is: (a) compliant with at least one of the Gulf Cooperation Council Standardization Organization GSO 2231/2012, GSO 839/1997, or GSO 1863/2013 standard; or (b) Halal certified, Kosher certified, or HACCP certified.

Aspect 78. The process for converting plastic waste according to Aspect 76, wherein the antioxidant comprises, consists essentially of, or is a hindered phenol, a metal salt of a hindered phenol, an oil-soluble polymetal organic compound, a hindered phenylenediamine compound, or a combination thereof.

Aspect 79. The process for converting plastic waste according to Aspect 76, wherein the antioxidant comprises, consists essentially of, or is diphenylamines, phenyl naphthylamines, phenothiazines, imidodibenzyls, diphenyl phenylene diamines, aromatic amines, or any combination thereof.

Aspect 80. The process for converting plastic waste according to Aspect 76, wherein the antioxidant comprises, consists essentially of, or is 2-t-butyl-4-heptyl phenol, 2-t-butyl-4-octyl phenol, 2-t-butyl-4-dodecyl phenol, 2,6-di-t-butyl-4-methylphenol, 2,6-di-t-butyl-4-heptyl phenol, 2,6-di-t-butyl-4-dodecyl phenol, 2-methyl-6-t-butyl-4-heptyl phenol, 2-methyl-6-t-butyl-4-dodecyl phenol, 2,6-di-alkyl-phenolic propionic ester derivatives, 2,2'-bis(4-heptyl-6-t-butyl-phenol), 2,2'-bis(4-octyl-6-t-butyl-phenol), 2,2'-bis(4-dodecyl-6-t-butyl-phenol), 4,4'-bis(2,6-di-t-butyl phenol), 4,4'-methylene-bis(2,6-di-t-butyl phenol), 2-t-butyl-4-methoxyphenol, 3-t-butyl-4-methoxyphenol, propyl gallate, 2-(1,1-dimethylethyl)-1,4-benzenediol, p,p'-dioctyldiphenylamine, t-octylphenyl-α-naphthylamine, phenyl-α-naphthylamine, p-octylphenyl-α-naphthylamine, or any combination thereof.

Aspect 81. The process for converting plastic waste according to Aspect 76, wherein the antioxidant comprises, consists essentially of, or is olive plant materials, olive oil, olive leaf extracts, a sesame-based antioxidant, sesamol, sesamin, sesamolin, hydroxytyrosol, tyrosol, caffeic acid, ferulic acid, alkannin, shikonin, carnosic acid, carnosic acid-EDTA, α-tocopherol (TCP), propyl gallate (PG), 1-ascorbic acid 6-palmitate (AP), gallic acid, quercetin, myricetin, catechin, genistein, isoflavones, flavanols, cinnamic acid, hydroxycinnamic acid, oleuropein, oryzanols, tocols, β-carotene, carotenoids, lycopene, marigold, paprika, bixin, or any combination thereof.

Aspect 82. The process for converting plastic waste according to Aspect 76, wherein the antioxidant comprises, consists essentially of, or is an antioxidant derived from olive plant material, olive oil mill waste, ajowan (*Carum copticum*), tinctoria roots, rosemary extract, *Guiera senegalensis, Combretum hartmannianum, Majorana syriaca*, sesame, Artmisia *scoparia, Cinnamomum cassia*, rosemary (Rosemarinus *officinalis*), clove (Syzygium *aromaticum*), cinnamon (*Cinnamomum zeylanicum*), broccoli, citrus, chemlali olive, defatted rice brand, bene hull oil (unsaponifiable matter), oregano, green tea, Cortex *fraxini, Polygonum cuspidatum*, marigold, *Capsicum annuum*, and garlic.

Aspect 83. The process for converting plastic waste according to any of the preceding Aspects, further comprising contacting the process feed in the first heating zone with a chemically-modified solid oxide comprising or consisting essentially of a solid oxide treated with an electron-withdrawing anion, in the presence or the absence of the hydrocarbon co-feed.

Aspect 84. The process for converting plastic waste according to any of the preceding Aspects, further comprising heating the process feed in the first heating zone in the presence of a chemically-modified solid oxide comprising or consisting essentially of a solid oxide treated with an electron-withdrawing anion, in the presence or the absence of the hydrocarbon co-feed.

Aspect 85. The process for converting plastic waste according to any of the preceding Aspects, further comprising contacting the reactor feed with an independently selected chemically-modified solid oxide, each comprising or consisting essentially of a solid oxide treated with an electron-withdrawing anion.

Aspect 86. The process for converting plastic waste according to any of the preceding Aspects, further comprising heating the reactor feed in the first heating zone, the second heating zone, or both the first heating zone and the second heating zone in the presence of an independently selected chemically-modified solid oxide, each comprising or consisting essentially of a solid oxide treated with an electron-withdrawing anion.

Aspect 87. The process for converting plastic waste according to any of the preceding Aspects, wherein the depolymerization catalyst further comprises a chemically-modified solid oxide, comprising or consisting essentially of a solid oxide treated with an electron-withdrawing anion.

Aspect 88. The process for converting plastic waste according to any of Aspects 83-87, wherein the chemically-modified solid oxide is generated by treatment of a solid oxide with an acid of an electron-withdrawing anion or a salt of an electron-withdrawing anion.

Aspect 89. The process for converting plastic waste according to Aspect 88, wherein following treatment of the solid oxide with the acid or the salt of an electron-withdrawing anion, the chemically-modified solid oxide is dried and calcined.

Aspect 90. The process for converting plastic waste according to any of Aspects 83-89, wherein the solid oxide of the chemically-modified solid oxide comprises, consists essentially of, or is $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof (for example, silica-alumina), and any combination thereof.

Aspect 91. The process for converting plastic waste according to any of Aspects 83-89, wherein the solid oxide of the chemically-modified solid oxide comprises, consists essentially of, or is silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

Aspect 92. The process for converting plastic waste according to any of Aspects 83-91, wherein the electron-withdrawing anion of the chemically-modified solid oxide comprises, consists essentially of, or is sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof.

Aspect 93. The process for converting plastic waste according to any of Aspects 83-92, wherein the chemically-modified solid oxide is generated by treatment of a solid oxide with sulfuric acid, sulfate ion, bisulfate ion, fluoro sulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

Aspect 94. The process for converting plastic waste according to any of Aspects 83-93, wherein the chemically-modified solid oxide comprises a sulfur oxoacid anion-modified solid oxide, a phosphorus oxoacid anion-modified solid oxide, or a halide ion-modified solid oxide.

Aspect 95. The process for converting plastic waste according to any of Aspects 83-94, wherein the chemically-modified solid oxide comprises a sulfated solid oxide, bisulfated (hydrogen sulfated) solid oxide, fluoro sulfated solid oxide, phosphated solid oxide, fluorophosphated solid oxide, fluorided solid oxide, or chlorided solid oxide.

Aspect 96. The process for converting plastic waste according to any of Aspects 83-95, wherein:
the solid oxide of the chemically-modified solid oxide comprises, consists essentially of, or is silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and
the electron-withdrawing anion of the chemically-modified solid oxide comprises, consists essentially of, or is sulfate, bisulfate, fluorosulfate, phosphate, fluorophosphates, fluoride, or chloride.

Aspect 97. The process for converting plastic waste according to any of Aspects 83-96, wherein the chemically-modified solid oxide comprises or consists essentially of sulfated alumina, sulfated silica-alumina, or sulfated silica-coated alumina.

Aspect 98. The process for converting plastic waste according to any of Aspects 83-97, wherein the chemically-modified solid oxide is metal-treated with a metal cation selected from a Group 1, 2, 12, or 13 metal.

Aspect 99. The process for converting plastic waste according to any of the preceding Aspects, wherein one or more output streams comprises halogenated hydrocarbons in a first concentration, and further comprising contacting the one or more output streams with a dehydrohalogenation catalyst to reduce the first concentration of halogenated hydrocarbons to a second concentration.

Aspect 100. The process for converting plastic waste according to Aspect 99, wherein the dehydrohalogenation catalyst comprises, consists essentially of, or is a Group 4-13 metal supported on a metal oxide or aluminosilicate support, or a Group 6-11 metal supported on a metal oxide or aluminosilicate support.

Aspect 101. The process for converting plastic waste according to any of Aspects 99-100, wherein the dehydrohalogenation catalyst comprises chromium, molybdenum, tungsten, iron, ruthenium, osmium, cobalt, rhodium, iridium, nickel, palladium, platinum, zinc, magnesium, gallium, titanium, tantalum, or any combination thereof, supported on alumina, silica, silica-alumina, silica-coated alumina, titania, zirconia, a zeolite, a molecular sieve, aluminophosphate, or a combination thereof.

Aspect 102. The process for converting plastic waste according to any of the preceding Aspects, wherein the plurality of output streams comprise a light hydrocarbon stream, a medium hydrocarbon stream, a heavy hydrocarbon stream, or any combination thereof.

Aspect 103. The process for converting plastic waste according to any of the preceding Aspects, wherein one of the plurality of output streams comprises $C_2$-$C_5$ saturated hydrocarbons.

Aspect 104. The process for converting plastic waste according to Aspect 103, wherein the output stream further comprises $C_2$-$C_5$ unsaturated hydrocarbons.

Aspect 105. The process for converting plastic waste according to any of the preceding Aspects, wherein one of the plurality of output streams comprises $C_6$-$C_8$ saturated hydrocarbons.

Aspect 106. The process for converting plastic waste according to Aspect 105, wherein the output stream further comprises $C_6$-$C_8$ unsaturated hydrocarbons.

Aspect 107. The process for converting plastic waste according to any of the preceding Aspects, wherein one of the plurality of output streams comprises $C_{9+}$ hydrocarbons.

Aspect 108. The process for converting plastic waste according to any of the preceding Aspects, wherein the plurality of output streams comprise a $C_2$-$C_5$ hydrocarbon stream, a $C_6$-$C_8$ hydrocarbon stream, and a heavy ($C_{9+}$) hydrocarbon stream.

Aspect 109. The process for converting plastic waste according to any of the preceding Aspects, wherein one output stream comprises $C_2$-$C_5$ hydrocarbons and halogenated hydrocarbons, and further comprising dehalogenation of the halogenated hydrocarbons.

Aspect 110. The process for converting plastic waste according to any of the preceding Aspects, wherein one output stream comprises $C_6$-$C_8$ hydrocarbons and halogenated hydrocarbons, and further comprising dehalogenation of the halogenated hydrocarbons.

Aspect 111. The process for converting plastic waste according to any of the preceding Aspects, wherein one output stream comprises $C_2$-$C_5$ hydrocarbons, and further comprising providing the $C_2$-$C_5$ hydrocarbons to a steam cracker to produce a stream cracker effluent comprising circular ethylene and/or circular propylene.

Aspect 112. The process for converting plastic waste according to any of the preceding Aspects, wherein one output stream comprises $C_6$-$C_8$ hydrocarbons, and further comprising providing the $C_6$-$C_8$ hydrocarbons to a reforming unit or an AROMAX® unit to produce one or more circular aromatic products.

Aspect 113. The process for converting plastic waste according to any of the preceding Aspects, wherein one output stream comprises $C_6$-$C_8$ hydrocarbons, and further comprising providing the $C_6$-$C_8$ hydrocarbons to a steam cracker to produce a stream cracker effluent comprising circular ethylene and/or circular propylene.

Aspect 114. A system for converting plastic waste, the system comprising:
(a) a first heating zone configured to receive a process feed and optionally receive a first hydrocarbon co-feed, and heat the process feed to provide a reactor feed;
(b) a depolymerization reactor comprising a first feed inlet configured to receive the reactor feed, a second heating zone, and at least one outlet configured to discharge a reactor effluent, and configured to contact the reactor feed with a depolymerization catalyst under depolymerization conditions; and
(c) a separation unit, configured to receive and separate the reactor effluent into a plurality of output streams, each output stream comprising a circular product.

Aspect 115. The system for converting plastic waste according to Aspect 114, wherein the first heating zone comprises an extruder.

Aspect 116. The system for converting plastic waste according to any of Aspects 114-115, wherein the first heating zone further comprises a mixer configured to mix the process feed and the hydrocarbon co-feed to provide a reactor feed.

Aspect 117. The system for converting plastic waste according to any of Aspects 114-116, wherein the depolymerization reactor further comprises a second feed inlet configured to receive a second hydrocarbon co-feed, wherein the second hydrocarbon co-feed is the same or different from the first hydrocarbon co-feed.

Aspect 118. The system for converting plastic waste according to any of Aspects 114-117, wherein the depolymerization reactor comprises a first outlet configured to discharge a gaseous reactor effluent and a second outlet configured to discharge a liquid reactor effluent.

Aspect 119. The system for converting plastic waste according to any of Aspects 114-118, wherein the separation unit comprises one or more condensers downstream of the depolymerization unit configured to separate the reactor effluent into the plurality of output streams.

Aspect 120. The system for converting plastic waste according to any of Aspects 114-119, wherein the separation unit is configured to separate the reactor effluent into a light hydrocarbon stream comprising $C_2$-$C_5$ hydrocarbons, a medium hydrocarbon stream comprising $C_6$-$C_8$ hydrocarbons, and a heavy hydrocarbon stream comprising $C_{9+}$ hydrocarbons.

Aspect 121. The system for converting plastic waste according to any of Aspects 114-120, wherein the separation unit is configured to provide a $C_2$-$C_5$ hydrocarbon stream, the system further comprising a steam cracker configured to receive the $C_2$-$C_5$ hydrocarbon stream and produce a stream cracker effluent comprising circular ethylene and/or circular propylene.

Aspect 122. The system for converting plastic waste according to any of Aspects 114-121, wherein the separation unit is configured to provide a $C_6$-$C_8$ hydrocarbon stream, the system further comprising a steam cracker configured to receive the $C_6$-$C_8$ hydrocarbon stream and produce a stream cracker effluent comprising circular ethylene and/or circular propylene.

Aspect 123. The system for converting plastic waste according to any of Aspects 114-122, wherein the separation unit is configured to provide a $C_6$-$C_8$ hydrocarbon stream, the system further comprising an AROMAX® unit or a reforming unit configured to receive the $C_6$-$C_8$ hydrocarbon stream and produce one or more circular aromatic products.

Aspect 124. The system for converting plastic waste according to any of Aspects 114-123, wherein the separation unit is configured to provide a $C_{9+}$ hydrocarbon stream, the system further comprising a fluid catalytic cracker (FCC) configured to receive the $C_{9+}$ stream and produce an FCC effluent comprising circular naphtha ($C_6$-$C_{10}$ hydrocarbons) and circular $C_5$ and lighter ($C_{5-}$) hydrocarbons.

Aspect 125. The system for converting plastic waste according to Aspect 114, wherein the system further comprises a pretreater between the separation unit and the fluid catalytic cracker (FCC) configured to receive the $C_{9+}$ stream and form a treated $C_{9+}$ stream having a lower sulfur, halogen, or aromatic content as compared with the $C_{9+}$ stream prior to pretreating.

Aspect 126. The system for converting plastic waste according to any of Aspects 114-125, wherein the separation unit is configured to provide a heavy hydrocarbon stream, the system further comprising a recycle pump and recycle line from the separation unit to the depolymerization reactor to return at least a portion of the heavy hydrocarbon stream from the separation unit to the depolymerization reactor.

Aspect 127. The system for converting plastic waste according to any of Aspects 114-126, the system further comprising a dehydrohalogenation unit downstream of the separation unit configured to receive any one of the plurality of output streams and reduce the halogen concentration therein.

Aspect 128. A process for converting plastic waste, the process comprising:
(a) providing a process feed comprising a polyolefin waste to a first heating zone and heating the process feed in the presence of a chemically-modified solid oxide comprising a solid oxide treated with an electron-withdrawing anion;
(b) combining a hydrocarbon co-feed with the process feed to form a reactor feed;
(c) providing the reactor feed to a second heating zone and heating the reactor feed in the presence of a depolymerization catalyst under depolymerization conditions to form a reactor effluent; and
(d) separating the reactor effluent into a plurality of output streams, each output stream comprising a circular product.

What is claimed is:

1. A process for converting plastic waste, the process comprising:
   (a) providing a process feed comprising a polyolefin waste to a first heating zone and heating the process feed in the presence of a chemically-modified solid oxide comprising a solid oxide treated with an electron-withdrawing anion;
   (b) combining a hydrocarbon co-feed with the process feed to form a reactor feed;
   (c) providing the reactor feed to a second heating zone and contacting the reactor feed and a depolymerization catalyst under depolymerization conditions to form a reactor effluent; and
   (d) separating the reactor effluent into a plurality of output streams, each output stream comprising a circular product.

2. The process for converting plastic waste according to claim 1, wherein combining the hydrocarbon co-feed with the process feed occurs before, during, or after heating the process feed, or any combination thereof.

3. The process for converting plastic waste according to claim 1, wherein the first heating zone comprises an extruder, and the second heating zone comprises a fixed bed reactor or a fluidized bed reactor.

4. The process for converting plastic waste according to claim 1, wherein the process feed optionally further comprises additional plastic waste which is different from the polyolefin waste, and wherein the amount or the fraction of the circular product attributable to the polyolefin waste or the optional additional plastic waste in one or more output streams is determined by mass balance.

5. The process for converting plastic waste according to claim 1, wherein the process feed optionally further comprises additional plastic waste which is different from the polyolefin waste, and wherein the process further comprises certifying the circular product attributable to the polyolefin waste or the additional plastic waste in one or more output streams as Circular in accordance with International Sustainability and Carbon Certification (ISCC) standards, based upon the amount or the fraction of the circular product attributable to the polyolefin waste or the additional plastic waste in one or more output streams determined by mass balance and the free attribution method.

6. The process for converting plastic waste according to claim 1, wherein the process feed is heated in the first heating zone to a temperature of from 150° F. (66° C.) to 350° F. (177° C.), or to a temperature that is 15° F. (8° C.) to 50° F. (28° C.) below the boiling temperature of the hydrocarbon co-feed.

7. The process for converting plastic waste according to claim 1, wherein the depolymerization conditions comprise heating the reactor feed and the depolymerization catalyst in the second heating zone to a temperature of from 300° F. (149° C.) to 1,000° F. (538° C.).

8. The process for converting plastic waste according to claim 1, wherein depolymerization conditions comprise heating the reactor feed and the depolymerization catalyst in the second heating zone in the presence of hydrogen at a pressure of from about 5 psig (34 kPa) to about 1,000 psig (6895 kPa).

9. The process for converting plastic waste according to claim 1, wherein the chlorine concentration or the fluorine concentration by weight in the reactor feed are, independently, less than 100 ppm.

10. The process for converting plastic waste according to claim 1, wherein the depolymerization catalyst comprises a zeolite-based catalyst, and a halogen concentration in the process feed, the hydrocarbon co-feed, or the reactor feed are controlled to provide (a) a chloride concentration in the zeolite-based catalyst of from 0.1 wt. % to 4.0 wt. %, (b) a fluoride concentration in the zeolite-based catalyst of from 0.1 wt. % to 5.0 wt. %, or both conditions (a) and (b).

11. The process for converting plastic waste according to claim 1, wherein the polyolefin waste comprises polyethylene, polypropylene, polystyrene, or any combination thereof.

12. The process for converting plastic waste according to claim 1, wherein the process feed is present in the reactor feed in a concentration of from 15 wt. % to 80 wt. %.

13. The process for converting plastic waste according to claim 1, wherein the reactor feed further comprises a waste plastic other than the polyolefin waste comprising polyester, polyamide, polyurethane, polyphenol, polycarbonate, polyvinyl halide, or any combination thereof.

14. The process for converting plastic waste according to claim 1, wherein the reactor feed further comprises a waste plastic other than the polyolefin waste comprising polyethylene terephthalate (PET) or polyvinyl chloride (PVC).

15. The process for converting plastic waste according to claim 1, wherein the hydrocarbon co-feed comprises a petroleum-based co-feed, a fossil fuel-based co-feed, or a bio-based co-feed.

16. The process for converting plastic waste according to claim 1, wherein the hydrocarbon co-feed comprises a pyrolysis oil, a $C_5$-$C_6$ saturated hydrocarbon, natural gas liquids (NGL), light naphtha, heavy naphtha, or combinations thereof.

17. The process for converting plastic waste according to claim 1, wherein the hydrocarbon co-feed comprises a pyrolysis oil, and wherein the pyrolysis oil is derived from pyrolysis of polyethylene, polypropylene, polystyrene, polyethylene terephthalate (PET), polyvinyl chloride (PVC), polyamide, polycarbonate, polyurethane, polyester, copolymers thereof, filled polymers thereof, composites thereof, natural or synthetic rubber, tires, or any combination thereof.

18. The process for converting plastic waste according to claim 1, wherein a natural or a synthetic antioxidant is combined with the hydrocarbon co-feed or the reactor feed.

19. The process for converting plastic waste according to claim 1, wherein the depolymerization catalyst comprises a zeolite-based catalyst, a chromia-based catalyst, or a combination thereof.

20. The process for converting plastic waste according to claim 1, wherein the depolymerization catalyst comprises a zeolite-based catalyst, and the zeolite-based catalyst comprises L-Zeolite (Zeolite L or LTL), X-Zeolite (Zeolite X), Y-Zeolite (Zeolite Y), omega Zeolite, beta Zeolite, SAPO-34 Zeolite, USY Zeolite, HY Zeolite, ZSM-4, ZSM-5 (MFI), ZSM-10, ZSM-11, ZSM-12, ZSM-20, ZSM-22, ZSM-23, ZSM-34, ZSM-35, ZSM-50, REY, USY, RE-USY, LZ-210, LZ-210-A, LZ-210-M, LZ-210-T, SSZ-13, SSZ-24, SSZ-26, SSZ-31, SSZ-33, SSZ-35, SSZ-37, SSZ-41, SSZ-42, SSZ-44, MCM-58, H-MOR (H-mordenite), mazzite, faujasite, chabazite, a modified mesoporous form thereof, or any combination thereof.

21. The process for converting plastic waste according to claim 1, wherein the depolymerization catalyst comprises a zeolite-based catalyst, and the zeolite-based catalyst comprises chromium, molybdenum, tungsten, iron, ruthenium, osmium, cobalt, rhodium, iridium, nickel, palladium, platinum, zinc, magnesium, gallium, titanium, tantalum, or any combination thereof.

22. The process for converting plastic waste according to claim 1, wherein the depolymerization catalyst comprises a zeolite-based catalyst, and the zeolite-based catalyst comprises Pt-L-Zeolite, Pt-ZSM-5, Pt—Y zeolite, Pt-SAPO-34 zeolite, Pt-USY zeolite, Pt-HY zeolite, Pt-beta zeolite, or any combination thereof.

23. The process for converting plastic waste according to claim 1, wherein the depolymerization catalyst comprises a zeolite-based catalyst, and the zeolite-based catalyst further comprises a promoter selected from a Group 1, 2, 14 or 15 metal.

24. The process for converting plastic waste according to claim 1, wherein the depolymerization catalyst comprises a zeolite-based catalyst, and the zeolite-based catalyst comprises a promoter selected from tin or bismuth.

25. The process for converting plastic waste according to claim 1, further comprising contacting the reactor feed under depolymerization conditions with a non-zeolite cracking catalyst comprising a clay, an acid treated clay, a perovskite, a layered titanate, silica alumina, silica-coated alumina, acidic alumina, tungstated zirconia, activated carbon, natural kaolin, acid-modified kaolin, bentonite, or any combination thereof.

26. The process for converting plastic waste according to claim 1, wherein the depolymerization catalyst comprises a zeolite-based catalyst, and the zeolite-based catalyst is characterized by (a) a zeolite pore volume of from about 0.10 mL/g to about 2.0 mL/g, (b) a catalyst surface area of from about 100 $m^2$/g to about 1,000 $m^2$/g, (c) a zeolite pore diameter of from about 4.0 Å (0.4 nm) to about 10 Å (1 nm), or (d) any combination thereof.

27. The process for converting plastic waste according to claim 1, wherein the depolymerization catalyst comprises a zeolite-based catalyst, and the zeolite-based catalyst is in particulate form having an average particle size of from about 2 μm to about 300 μm, or from about 5 μm to about 200 μm.

28. The process for converting plastic waste according to claim 1, wherein the solid oxide of the chemically-modified solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

29. The process for converting plastic waste according to claim 1, wherein the solid oxide is treated with an electron-withdrawing anion comprising sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof.

30. The process for converting plastic waste according to claim 1, wherein:
the solid oxide of the chemically-modified solid oxide is selected from silica, alumina, silica-alumina, silica-coated alumina, aluminum phosphate, aluminophosphate, heteropolytungstate, titania, zirconia, magnesia, boria, zinc oxide, a mixed oxide thereof, or any combination thereof; and
the solid oxide is treated with an electron-withdrawing anion selected from sulfate, bisulfate, fluorosulfate, phosphate, fluorophosphates, fluoride, or chloride.

31. The process for converting plastic waste according to claim 1, wherein the chemically-modified solid oxide comprises sulfated alumina, sulfated silica-alumina, or sulfated silica-coated alumina.

32. The process for converting plastic waste according to claim 1, wherein the chemically-modified solid oxide is metal-treated with a metal cation selected from a Group 1, 2, 12, or 13 metal.

33. The process for converting plastic waste according to claim 1, further comprising contacting the reactor feed in the second heating zone with a chemically-modified solid oxide comprising a solid oxide treated with an electron-withdrawing anion.

34. The process for converting plastic waste according to claim 1, wherein the plurality of output streams comprise a light ($C_2$-$C_5$) hydrocarbon stream, a medium ($C_6$-$C_8$) hydrocarbon stream, a heavy ($C_{9+}$) hydrocarbon stream, or any combination thereof.

35. The process for converting plastic waste according to claim 1, further comprising contacting any of the plurality of output streams with a dehydrohalogenation catalyst to reduce a halogen concentration in the output stream.

36. The process for converting plastic waste according to claim 1, wherein one output stream comprises $C_2$-$C_5$ hydrocarbons, and further comprising providing the $C_2$-$C_5$ hydrocarbons to a steam cracker to produce a stream cracker effluent comprising circular ethylene or circular propylene.

37. The process for converting plastic waste according to claim 1, wherein one output stream comprises $C_6$-$C_8$ hydrocarbons, and further comprising (a) providing the $C_6$-$C_8$ hydrocarbons to a steam cracker to produce a stream cracker effluent comprising circular ethylene or circular propylene, or (b) providing the $C_6$-$C_8$ hydrocarbons to a reforming unit or an AROMAX® unit to produce one or more circular aromatic products.

38. The process for converting plastic waste according to claim 1, wherein one output stream comprises $C_{9+}$ hydrocarbons, and further comprising recycled the $C_{9+}$ hydrocarbons to the second heating zone.

\* \* \* \* \*